US007927595B1

(12) United States Patent
June et al.

(10) Patent No.: US 7,927,595 B1
(45) Date of Patent: Apr. 19, 2011

(54) METHODS FOR DOWNREGULATING CCR5 IN T CELLS WITH ANTI-CD3 ANTIBODIES AND ANTI-CD28 ANTIBODIES

(75) Inventors: Carl H. June, Rockville, MD (US); Richard G. Carroll, Gaithersburg, MD (US); James L. Riley, Elkridge, MD (US); Daniel C. St. Louis, Rockville, MD (US); Bruce L. Levine, Cherry Hill, NJ (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/027,205

(22) Filed: Feb. 20, 1998

Related U.S. Application Data

(60) Provisional application No. 60/037,422, filed on Feb. 21, 1997.

(51) Int. Cl.
*A61K 39/395* (2006.01)
*C07K 16/28* (2006.01)

(52) U.S. Cl. ............... 424/154.1; 424/130.1; 424/143.1; 424/144.1; 424/153.1; 424/173.1; 530/387.1; 530/388.1; 530/388.2; 530/388.7; 530/388.75

(58) Field of Classification Search ............... 424/130.1, 424/141.1, 153.1, 144.1, 178.1; 435/375; 530/387.1, 388.22, 388.75, 391.1
See application file for complete search history.

(56) References Cited

U.S. PATENT DOCUMENTS

| 5,561,047 | A * | 10/1996 | Shattil |
| 6,129,916 | A * | 10/2000 | Chang |
| 6,352,694 | B1 * | 3/2002 | June et al. |
| 6,569,997 | B1 * | 5/2003 | Kwon ............ 530/388.22 |
| 6,905,680 | B2 * | 6/2005 | June et al. ............ 424/93.71 |
| 2004/0086528 | A1 * | 5/2004 | Allaway et al. ............ 424/208.1 |

FOREIGN PATENT DOCUMENTS

WO   WO 95/33823   * 12/1995

OTHER PUBLICATIONS

Riley et al. J. Virol. 72:8273-8280 1998.*
Carroll et al. Immunol. 10:195-202 1998.*
Creson et al. J. Virol. 1999; 73(11):9337-9347.*
Spina et al. J. Clin. Invest. 1997; 99:1774-1785.*
Alkhatib, G. et al. "CC CKR5: A Rantes, MIP-1α, MIP-1β Receptor as a Fusion Cofactor for Macrophage-Tropic HIV-1" *Science* 272:1955-1958 (1996).
Åsjö, B. et al. "A Novel Mode of Human Immunodeficiency Virus Type 1 (HIV-1) Activation: Ligation of CD28 Alone Induces HIV-1 Replication in Naturally Infected Lymphocytes" *Journal of Virology* 67(7):4395-4398 (1993).
Baca, L.M. et al. "Regulation of Interferon-α-Inducible Cellular Genes in Human Immunodeficiency Virus-Infected Monocytes" *Journal of Leukocyte Biology* 55:299-309 (1994).

Baier, M. et al. "HIV Suppression by Interleukin-16" *Nature* 378:563 (1995).
Barker, T.D. et al. "Identification of Multiple and Distinct $CD8^+$ T Cell Suppressor Activities" *The Journal of Immunology* 156:4476-4483 (1996).
Beyers, A.D. et al. "Molecular Associations Between the T-Lymphocyte Antigen Receptor Complex and the Surface Antigens CD2, CD4, or CD8 and CD5" *Immunology* 89:2945-2949 (1992).
Brand, D. et al. "Determinants of Human Immunodeficiency Virus Type 1 Entry in the CDR2 Loop of the CD4 Glycoprotein" *Journal of Virology* 69(1):166-171 (1995).
Breitmeyer, J.B. et al. "The T11 (CD2) Molecule is Functionally Linked to the T3/Ti T Cell Receptor in the Majority of T Cells" *The Journal of Immunology* 139:2899 (1987).
Ceuppens, J.L. and Baroja, M.L. "Monoclonal Antibodies to the CD5 Antigen Can Provide the Necessary Second Signal for Activation of Isolated Resting T Cells by Solid-Phase-Bound OKT3" *The Journal of Immunology* 137:1816-1821 (1986).
Choe, H. et al. "The β-Chemokine Receptors CCR3 and CCr5 Facilitate Infection by Primary HIV-1 Isolates" *Cell* 85:1135-1148 (1996).
Cocchi, F. et al. "Identification of Ranted, MIP-1α, and MIP-1β as the Major HIV-Suppressive Factors Produced by $CD8^+$ T Cells" *Science* 270:1811-1815 (1995).
Conlon, K. et al. "$CD8^+$ and $CD45RA^+$ human Peripheral Blood Lymphocytes are Potent Sources of Macrophage Inflammatory Protein 1α, Interleukin-8 and RANTES" *Eur. J. Immunol.* 25:751-756 (1995).
Dean, M. et al. "Genetic Restriction of HIV-1 Infection and Progression to AIDS by a Deletion Allele of the *CKR5* Structural Gene" *Science* 273:1856-1862 (1996).
Deng, H. et al. "Identification of a Major Co-Receptor for Primary Isolates of HIV-1" *Nature* 381:661-666 (1996).
Doranz, B.J. et al. "A Dual-Tropic Primary HIV-1 Isolate That Uses Fusin and the β-Chemokine Receptors CKR-5, CKR-3, and CKR-2b as Fusion Cofactors" *Cell* 85:1149-1158 (1996). Dragic, T. et al. "HIV-1 Entry Into $CD4^+$ Cells is Mediated by the Chemokine Receptor CC-CKR-5" *Nature* 381:667-673 (1996).
Fauci, A.S. "Host Factors and the Pathogenesis of HIV-Induced Disease" *Nature* 384:529-534 (1996).
Feng, Y. et al. "HIV-1 Entry Cofactor: Functional cDNA Cloning of a Seven-Transmembrane, G Protein-Coupled Receptor" *Science* 272:872-877 (1996).
Gartner, S. et al. "The Role of Mononuclear Phagocytes in HTLV-III/LAV Infection" *Science* 233:215-219 (1986).
Geppert, T.D. et al "Activation of Human T4 Cells by Cross-Linking Class I MHC Molecules" *The Journal of Immunology* 140:2155-2164 (1988).
Geppert, T.D and Lipsky, P.E. "Activation of T Lyphocytes by Immobilized Monoclonal Antibodies to CD3: Regulator Influences of Monoclonal Antibodies to Additional T Cell Surface Determinants" *J. Clin. Invest.* 81:1497-1505 (1988).

(Continued)

*Primary Examiner* — Phillip Gambel
(74) *Attorney, Agent, or Firm* — Joseph K. Hemby, Jr.; Ning Yang; Albert Churilla

(57) ABSTRACT

Methods for modulating HIV-1 fusion cofactor expression by manipulating an accessory molecule on the surface of T cells, such as CD28, are described. The invention encompasses methods for modulating HIV-1 fusion cofactor expression by stimulating or inhibiting one or more intracellular signals which result from ligation of a surface receptor on a T cell which binds a costimulatory molecule. In one embodiment, expression of an HIV-1 fusion cofactor, such as CCR5, is downregulated by stimulating a CD28-associated signal in the T cell.

11 Claims, 9 Drawing Sheets

OTHER PUBLICATIONS

Hansen, J.A. et al. "Monoclonal Antibodies Identifying a Novel T-Cell Antigen and Ia Antigens of Human Lymphocytes" *Immunogenetics* 10:247-260 (1980).

June, C.H. et al. "The B7 and CD28 Receptor Families" *Immunology Today* 15(7):321-331 (1994).

June, C.H. et al. "T-Cell Proliferation Involving the CD28 Pathway Is Associated with Cyclosporine-Resistant Interleukin 2 Gene Expression" *Molecular and Cellular Biology* 7(12):4472-4481 (1987).

Kabat, D. et al. "Differences in CD4 Dependence for Infectivity of Laboratory-Adapted and Primary Patient Isolates of Human Immunodeficiency Virus Type 1" *Journal of Virology* 68(4):2570-2577 (1994).

Kinter, A.L. et al. "Interleukin 2 Induces $CD8^+$ T Cell-Mediated Suppression of Human Immunodeficiency Virus Replication in $CD4^+$ T Cells and this Effect Overrides Its Ability to Stimulated Virus Expression" *Proc. Natl. Acad. Sci. USA* 92:10985-10989 (1995).

Kollmann, T. R. et al. "Inhibition of Acute in vivo Human Immunodeficiency Virus Infection by 7 Human Interleukin 10 Treatment of SCID Mice Implanted with Human Fetal Thymus and Liver" *Proc. Natl. Acad. Sci. USA* 93:3126-3131 (1996).

Lai, J-H and Tan, T-H. "CD28 Signaling Causes a sustained Down-Regulation of IκBα Which Be Prevented by the Immunosuppressant Rapamycin" *The Journal of Biological Chemistry* 269(48):30077-30080 (1994).

Ledbetter, J.A. et al. "Antibodies to Tp67 and Tp44 Augment and Sustain Proliferative Responses of Activated T Cells" *The Journal of Immunology* 135(4):2331-2336 (1985).

Ledbetter, J.A. et al. "An Immunoglobulin Light Chain Dimer with CD4 Antigen Specificity" *Mol. Immunol.* 24:1255-1261 (1987).

Ledbetter, J.A. et al. "Role of CD2 Cross-Linking in Cytoplasmic Calcium Responses and T Cell Activation" *Eur. J. Immunol.* 18:1601-1608 (1988).

Ledbetter, J.A. et al. "Signal Transduction Through CD4 Receptors: Stimulatory vs. Inhibitory Activity is Regulated by CD4 Proximity to the CD3/T Cell Receptor" *Eur. J. Immunol.* 18:525-532(1988).

Levine, B.L. et al. "Antiviral Effect and Ex Vivo $CD4^+$ T Cell Proliferation in HIV-Positive Patients as a Result of CD28 Costimulation" *Science* 272:1939-1943 (1996).

Levine, B.L. et al. "CD28 Ligands CD80 (B7-1) and CD86 (B7-2) Induce Long-Term Autocrine Growth of $CD4^+$ T Cells and Induce Similar Patterns of Cytokine Secretion in vitro" *International Immunology* 7(6):891-904 (1995).

Liu, R. et al. "Homozygous Defect in HIV-1 Coreceptor Accounts for Resistance of Some Multiply-Exposed Individuals to HIV-1 Infection" *Cell* 86:367-377 (1996).

Loetscher, P. et al. "Interleukin-2 Regulates CC Chemokine Receptor Expression and Chemotactic Responsiveness in T Lymphocytes" *J. Exp. Med.* 184:569-577 (1996).

Los, M. et al. "Inhibition of Activation of Transcription Factor AP-1 by CD28 Signalling in Human T-Cells" *Biochem. J.* 302:119-123 (1994).

Mackewicz, C.E. et al. "$CD8^+$ T Cells Suppress Human Immunodeficiency Virus Replication by Inhibiting Viral Transcription" *Proc. Natl. Acad. Sci. USA* 92:2308-2312 (1995).

Martin, P.J. et al. "A New Human T-Cell Differentiation Antigen: Unexpected Expression on Chronic Lymphocytic Leukemia Cells" *Immunogenetics* 11:429-439 (1980).

Mascola, J.R. et al. "Two Antigenically Distinct Subtypes of Human Immunodeficiency Virus Type 1: Viral Genotype Predicts Neutralization Serotype" *The Journal of Infectious Diseases* 169:48-54 (1994).

Meylan, P.R.A. et al. "Mechanisms for the Inhibition of HIV Replication by Interferons-60 , -62 , and -γ in Primary Human Macrophages" *Virology* 193:138-148 (1993).

Minty, A. et al. "Interleukin-13 is a New Human Lymphokine Regulating Inflammatory and Immune Responses" *Nature* 362:248-250 (1993).

Montaner, L.J. et al. "Interleukin 13 Inhibits Human Immunodeficiency Virus Type 1 Production in Primary Blood-Derived Human Macrophages In Vitro" *J. Exp. Med.* 178:743-747 (1993).

Paxton, W.A. et al. "Relative Resistance to HIV-1 Infection of CD4 Lymphocytes from Persons Who Remain Uninfected Despite Multiple High-Risk Sexual Exposures" *Nature Medicine* 2(4):412-417 (1996).

Pinchuk, L.M. et al. "The Role of CD40 and CD80 Accessory Cell Molecules in Dendritic Cell-Dependent HIV-1 Infection" *Immunity* 1:317-325 (1994).

Poli, G. et al. "Interferons in the Pathogenesis and Treatment of Human Immunodeficiency Virus Infection" *Antiviral Research* 24:221-233 (1994).

Schrezenmeier, H. and Fleischer, B. "A Regulatory role for the CD4 and CD8 Molecules in T Cell Activation" *The Journal of Immunology* 141(2):398-403 (1988).

Schwarz, M. et al. "High-Level IL-10 Production by Monoclonal Antibody-Stimulated Human T Cells" *Immunology* 86:364-371 (1995).

Smithgall, M.D. et al. "Costimulation of $CD4^+$ T Cells via CD28 Modulates Human Immunodeficiency Virus Type 1 Infection and Replication In Vitro" *AIDS Research and Human Retroviruses* 11(8):885-892 (1995).

Spira, A.I. and Ho, D.D. "Effect of Different Donor Cells on Human Immunodeficiency Virus Type 1 Replication and Selection in Vitro" *Journal of Virology* 69(1):422-429 (1995).

Thompson, C.B. et al. "CD28 Activation Pathway Regulates the Production of Multiple T-Cell-Derived Lymphokines/Cytokines" *Proc. Natl. Acad. Sci. USA* 86:1333-1337 (1989).

Vahey, M.T. and Wong, M.T. "Quantitative Liquid Hybrdization PCR Method Employing Storage Phosphor Technology" *PCR Primer: A Laboratory Manual*. C.W. Dieffenbach and G.S. Dveksler, eds. Cold Spring Harbor Laboratory Press:313-338 (1995).

Wainberg, M.A. et al. "Differential Susceptibility of Human Lymphocyte Cultures to Infection by HIV" *Clin. Exp. Immunol.* 70:136-142 (1987).

Walker, C.M. et al. "$CD8^+$ Lymphocytes Can Control HIV Infection in Vitro by Suppressing Virus Replication" *Science* 234:1563-1566 (1986).

Weissman, D. et al. "Interleukin 10 Blocks HIV Replication in Macrophages by Inhibiting the Autocrine Loop of Tumor Necrosis Factor α and Interleuking 6 Induction of Virus" *AIDS Research and Human Retroviruses* 10(10):1199-1206 (1994).

Roederer, M., P.A. Raju, D. K. Mitra, L. A. Herzenberg, and L. A. Herzenberg. 1997. HIV does not replicate in naïve CD4 T cells stimulated with CD3/CD28. J. Clin. Invest. 99:1555-1564. In figure 2 B and C they show that CD3/28 stimulation on plastic (not beads) increases HIV replication from memory CD4 cells.

Spina, C. A., H. E. Prince, and D. D. Richman. 1997. Preferential replication of HIV-1 in the CD45RO memory cell subset of primary CD4 lympocytes in vitro. J. Clin. Invest. 99:1774-1785. Many figures show cd3+28 soluble increasing HIV replication from cultures of human CD4 memory cells.

\* cited by examiner

A.

Probe: CXCR4 / Fusin

B.

Probe: CCR5

C.

Probe: 28S rRNA

METHODS FOR DOWNREGULATING CCR5 IN T CELLS WITH ANTI-CD3 ANTIBODIES AND ANTI-CD28 ANTIBODIES

RELATED APPLICATIONS

This application claims priority to U.S. provisional Application No. 60/037,422, filed on Feb. 21, 1997, the contents of which are incorporated herein by reference.

BACKGROUND OF THE INVENTION

A variety of immune factors influence the susceptibility of CD4 T cells to HIV-1 infection, including soluble factors and the state of T cell differentiation. Evidence for the importance of these host factors includes the observation that lymphocytes from different donors are not equally infectable with HIV-1, raising the possibility that resistance of lymphocytes to HIV I infection in vitro might be associated with different rates of disease progression (Spira, A. I. and D. D. Ho. 1995. *J. Virol.* 69:422; and Wainberg, M. A., N. Blain, and L. Fitz-Gibbon. 1987. *Clin. Exp. Immunol.* 70:136). Host factors that are recognized to affect the susceptibility of CD4 cells to HIV infection include factors intrinsic to the CD4 cell and indirect factors. Among the direct factors of recognized importance are CD4 and fusion coreceptors(s) expression. The density of CD4 receptors expressed on the cell surface influences the efficiency of HIV-1 infection (Kabat, D., 1994. J. Virol. 68:2570; and Brand, D., 1995. *J. Virol.* 69:166). Recently chemokine receptors have been identified as a critical determinant of susceptibility to infection with HIV-1. Macrophage-tropic strains of HIV-1 utilize CCR5 as a fusion cofactor (Alkhatib, G., 1996, *Science* 272:1955; Doranz, B. J., 1996 *Cell* 85:1149; Choe, H., 1996. *Cell* 85:1135; Dragic, T., 1996. *Nature* 381: Deng, H., 1996. *Nature* 381:661) while T cell tropic strains of HIV-1 employ CXCR4/fusin as a coreceptor (Feng, Y., 1996. *Science* 272:872). The importance of these coreceptors is illustrated by the recent observation that some multiply exposed individuals who remain uninfected with HIV-1 have mutations in CCR5 (Liu, R., 1996. *Cell* 86:367; Dean, M., 1996. *Science* 273:1856).

Indirect factors may also be important in determining the resistance of CD4 cells to HIV-1 infection. Most of the described effects have depended on CD8 cells. Levy and coworkers first reported that CD8 T cells from HIV-infected individuals were capable of suppressing endogenous viral replication at a transcriptional level in CD4 T cells from HIV-infected individuals (Walker, C. 1986. *Science* 234:1563). Suppression was mediated by a non-cytolytic, MHC-nonrestricted mechanism (Mackewicz, C. E., 1995. *Proc. Natl. Acad. Sci. U.S.A.* 92:2308). The C—C chemokines RANTES, MIP-1α, MIP-β have been shown to inhibit infection of M-tropic isolates, but not T cell tropic strains of HIV-1 (Cocchi, F., 1995. *Science* 270:1811). The potential importance of these findings were underscored by a report from Paxton and coworkers indicating that CD4 cells from people who were repeatedly exposed to HIV but remain uninfected, were resistant to infection with HIV (Paxton, W. A., 1996. *Nat. Med.* 2:412). They found that these resistant individuals secreted higher levels of C—C chemokines in vitro. Multiple distinct HIV-1 suppressive activities appear to be secreted or shed by CD8 cells (Barker, T. D., 1996. *J. Immunol.* 156:4476). IL-2 and IL-16 have also been proposed to inhibit HIV replication via CD8 cell mediated mechanisms (Kinter, A. L., 1995. *Proc. Natl. Acad. Sci. U.S.A.* 92:10985; Baier, M., A. 1995. Nature 378:563). IL-10 and TGF-β have also been shown to have inhibitory effects on HIV-1 replication (Fauci, A. S. 1996. *Nature* 384:529).

Recent studies have shown that while specificity of T cell activation is dictated by antigen receptor signals, effective activation requires at least one costimulatory signal. CD28 is the dominant costimulatory signal, and interaction of CD28 with its counter receptors CD80 or CD86 is required for the induction of many cellular immune responses (June, C. H., 1994. *Immunol. Today* 15:321). We recently reported that CD28 stimulation could mediate an antiviral effect (Levine, B. L., 1996. *Science* 272:1939). The effect was potent as CD4 cells from HIV-infected donors could be routinely propagated in culture without virus replication in the absence of antiretroviral drugs. The CD28-mediated effect was distinguished from previous reports in that the inhibition acted early in the viral life cycle and appeared to be independent of CD8 T cells.

SUMMARY OF THE INVENTION

This invention pertains to methods for modulating HIV-1 fusion cofactor expression by manipulating an accessory molecule on the surface of T cells, such as CD28 or CTLA-4. The invention encompasses methods for modulating HIV-1 fusion cofactor expression by stimulating or inhibiting one or more intracellular signals which result from ligation of a surface receptor on a T cell which binds a costimulatory molecule. In one embodiment, expression of an HIV-1 fusion cofactor, such as CCR5, is downregulated by stimulating a CD28-associated signal in the T cell.

The methods of the invention can be used to modulate HIV-1 fusion cofactor expression in vivo or ex vivo by stimulating or inhibiting one or more intracellular signals which result from ligation of a surface receptor on a T cell which binds a costimulatory molecule. In one embodiment, expression of an HIV-1 fusion cofactor, such as CCR5, is downregulated in vivo by administration of an agent, e.g., an anti-CD28 or an anti-CTLA-4 antibody, which stimulates or allows stimulation of a CD28-associated signal in a T cell of a subject. Alternatively, T cells can be obtained from a subject and contacted with an agent which stimulates (or allows stimulation of, e.g., a soluble CTLA4 antibody or fragment thereof, e.g., Fab fragment) a CD28-associated signal in the T cell to thereby inhibit or downregulate expression of an HIV-1 fusion cofactor ex vivo. Such methods are useful for the treatment of an individual having an HIV-1 infection, e.g., a chronic HIV-1 infection. In preferred embodiments, the agent is co-administered with another treatment, e.g., an influenza vaccine. The agent is administered in an amount effective to downregulate the HIV-1 fusion cofactor. In other preferred embodiments, the level of HIV-1 fusion cofactor expression is determined using, for example, Northern blot analysis, in situ hybridization, or cell staining. In yet further preferred embodiments, the level of viral load or viral burden in an HIV infected subject is determined following administration of an agent which stimulates or allows stimulation of a CD28-associated signal in the T cell.

The invention also pertains to compositions comprising an effective amount of an agent that downregulates an HIV-1 fusion cofactor, e.g., CCR5, expression by stimulating one or more intracellular signals which result from ligation of a surface receptor on a T cell which binds a costimulatory molecule (e.g., an anti-CD28 antibody, a B7-1 or a B7-2 ligand). Another embodiment of the invention pertains to compositions comprising an effective amount of an agent which allows stimulation of a CD28-associated signal in the T cell by, for example, blocking the interaction of B7 molecules with CTLA4 (e.g., CTLA4 antibodies or fragments thereof), thereby allowing B7 molecules to interact and stimulate a CD28-associated signal in the T cell. Such agents can be coupled to a solid phase surface (e.g., a biodegradable bead) which may additionally include an agent that provides a primary activation signal to the T cell (e.g., an anti-CD3 antibody) coupled to the same or different solid phase surface. Furthermore, the invention provides kits comprising the compositions, including instructions for use.

Another aspect of the invention pertains to screening assays for identifying inhibitors or activators of expression of an HIV-1 fusion cofactor, such as CCR5, in a cell following stimulation or inhibition of one or more intracellular signals which result from ligation of a surface receptor on the cell which binds a costimulatory molecule, such as CD28. In one embodiment, a T cell which expresses a cell surface receptor (e.g., CD28 or CTLA-4) which binds a costimulatory molecule is utilized. To identify an inhibitor of expression of an HIV-1 fusion cofactor, such as CCR5, an intracellular signal transduction pathway associated with the receptor in the T cell (e.g., CD28) is stimulated in the presence of an agent to be tested and an inhibitor is identified based upon its ability to inhibit or downregulate expression of the HIV-1 fusion cofactor in the T cell.

DETAILED DESCRIPTION OF THE INVENTION

Figure 1:
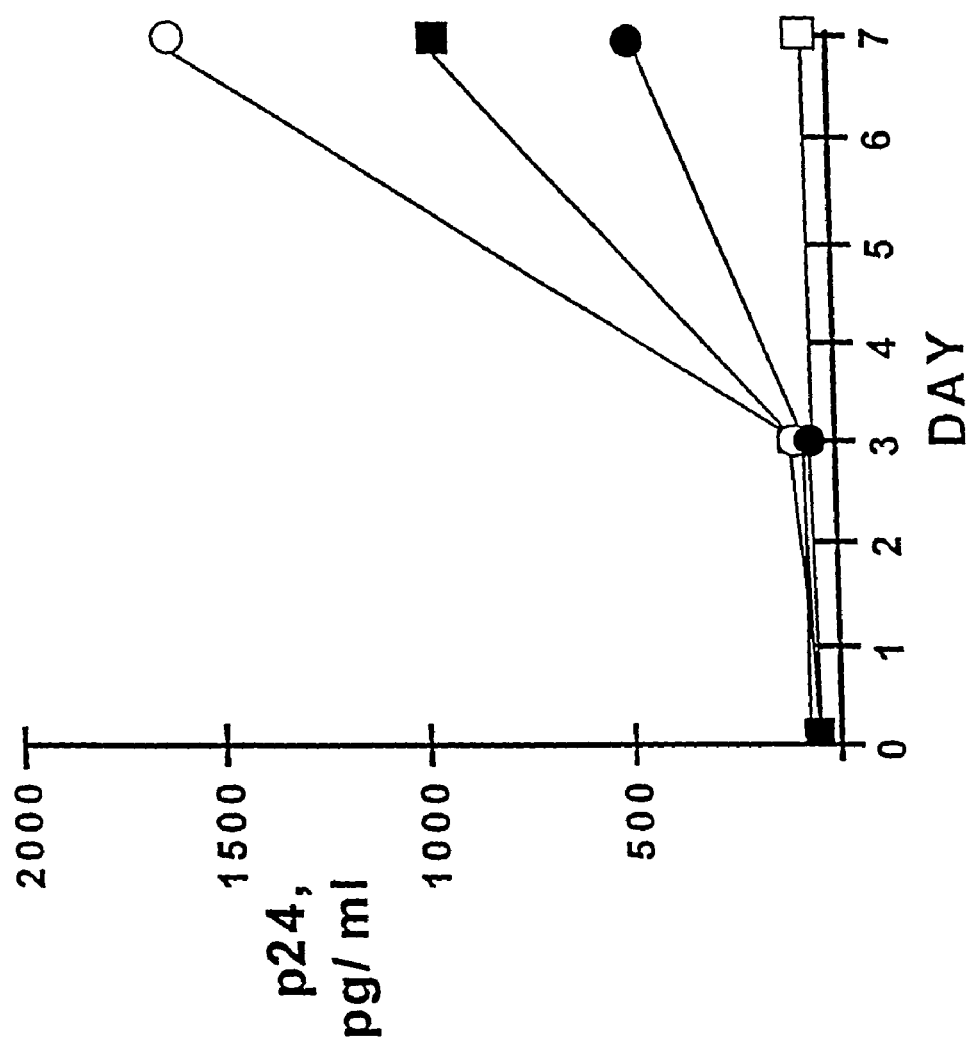
FIG. 1 is a graph depicting the presence of $p24_{Gag}$ antigen by ELISA in CD4 cells stimulated with αCD3/αCD28 (open symbols) or PHA/IL-2 (filled symbols) infected with $1 \times 10^4$ $TCID_{50}$ (median tissue culture infectious dose) of $HIV_{US1}$ (squares) or with $1 \times 10^4$ MAGI (18) infectious doses of $HIV_{NL4-3}$ (circles).

This invention pertains to methods for modulating HIV-1 fusion cofactor expression by manipulating an accessory molecule on the surface of T cells, such as CD28. The invention encompasses methods for modulating HIV-1 fusion cofactor expression by stimulating or inhibiting one or more intracellular signals which result from ligation of a surface receptor on a T cell which binds a costimulatory molecule. In one embodiment, expression of an HIV-1 fusion cofactor, such as CCR5, is downregulated by stimulating a CD28-associated signal in the T cell. In another embodiment, expression of an HIV-1 fusion cofactor, such as CCR5, is down-regulated by allowing stimulation of a CD28-associated signal in the T cell, by, for example, using an agent which blocks the interaction of B7 molecules (e.g., B7-1 and B7-2) with CTLA4, e.g., soluble CTLA4 antibodies or fragments thereof, thereby allowing B7 molecules to interact and stimulate a CD28-associated signal in the T cell.

Accordingly, one aspect of the invention pertains to methods for inhibiting or downregulating expression of an HIV-1 fusion cofactor (e.g., CCR5) by stimulating intracellular signal transduction associated with CD28 ligation. In one embodiment, an intracellular signal is stimulated by contacting a T cell expressing a CD28 cell surface receptor, such as a $CD4^+$ T cell, with an agent which acts extracellularly to stimulate a CD28-associated signal in the T cell (e.g., a ligand which binds CD28 or CTLA-4) or an agent which acts intracellularly to stimulate a CD28-associated signal in the T cell (e.g., an agent which stimulates production of D-3 phosphoinositides in the T cell, see e.g., PCT/US95/05213). The term "a T cell expressing a cell surface receptor that binds a costimulatory molecule" is intended to encompass T cells expressing CD28 and/or CTLA4, or other receptor capable of binding a costimulatory molecule such as B7-1, B7-2 or other B7 family member.

In one embodiment, stimulation of the accessory molecule CD28 is accomplished by contacting an activated population of T cells with a ligand which binds CD28. Activation of the T cells with, for example, an anti-CD3 antibody and stimulation of the CD28 accessory molecule results in proliferation of $CD4^+$ T cells. An anti-CD28 monoclonal antibody or fragment thereof capable of crosslinking the CD28 molecule, or a natural ligand for CD28 (e.g., a member of the B7 family of proteins, such as B7-1 (CD80) and B7-2 (CD86) (Freedman, A. S. et al. (1987) *J. Immunol.* 137:3260-3267; Freeman, G. J. et al. (1989) *J. Immunol.* 143:2714-2722; Freeman, G. J. et al. (1991) *J. Exp. Med.* 174:625-631; Freeman, G. J. et al. (1993) *Science* 262:909-911; Azuma, M. et al. (1993) *Nature* 366: 76-79; Freeman, G. J. et al. (1993) *J. Exp. Med.* 178:2185-2192)) can be used to induce stimulation of the CD28 molecule. In addition, binding homologues of a natural ligand, whether native or synthesized by chemical or recombinant technique, can also be used in accordance with the invention. Ligands useful for stimulating an accessory molecule can be used in soluble form, attached to the surface of a cell, or immobilized on a solid phase surface as described herein. Anti-CD28 antibodies or fragments thereof useful in stimulating proliferation of $CD4^+$ T cells include monoclonal antibody 9.3, an IgG2a antibody (Dr. Jeffery Ledbetter, Bristol Myers Squibb Corporation, Seattle, Wash.), monoclonal antibody KOLT-2, an IgG1 antibody, 15E8, an IgG1 antibody, 248.23.2, an IgM antibody and EX5.3D10, an IgG2a antibody. In one specific embodiment, the molecule providing the primary activation signal, for example a molecule which provides stimulation through the TCR/CD3 complex or CD2, and the costimulatory molecule are coupled to the same solid phase support. In particular, T cell activation and costimulation can be provided by a solid phase surface containing anti-CD3 and anti-CD28 antibodies.

In another embodiment, stimulation of the accessory molecule CD28 is accomplished by contacting an activated population of T cells with a ligand which binds CTLA-4. For example, anti-CTLA4 antibodies that cross react with CD28, e.g., 7G11 mAb, can be used. Such antibodies can be produced by techniques described below. In a preferred embodiment, the anti-CTLA4 antibody binds an epitope on CTLA4 which includes or encompasses an amino acid sequence:

$(Xaa)_n$-Pro-Pro-Tyr-Tyr-Leu-$(Xaa)_n$ (SEQ ID NO:1), wherein Xaa is any amino acid and n=0-20 (preferably 0-10, more preferably 0-5, even more preferably 0-3). This amino acid sequence is part of the binding site for B7-1 on the CTLA-4 receptor (as described in Harper K. et al. (1991) *J. Immunol.* 47:1037-1044). In native human CTLA4, this sequence is located at amino acid positions 101 to 105. Xaa can be additional CTLA4 amino acid residues flanking this region or can be other residues, e.g., included to enhance solubility or immunogenicity of the peptide. A peptide containing a common CD28/CTLA4 epitope (e.g., SEQ ID NO:1) can be used as an immunogen to raise an anti-CD28/CTLA4 antibody. The anti-CTLA-4 antibody can prevent the B7-1 and B7-2 ligands from binding to the CTLA-4 receptor, thereby allowing these ligands to bind to the CD28 receptor and stimulate a CD28-associated signal in the T cell.

In a specific embodiment of the invention, activated T cells are contacted with a stimulatory form of a natural ligand for CD28 for costimulation. The natural ligands of CD28 include the members of the B7 family of proteins, such as B7-1 (CD80) and B7-2 (CD86). B7-1 and B7-2 are collectively referred to herein as "B7 molecules". A "stimulatory form of a natural ligand for CD28" is a form of a natural ligand that is able to bind to CD28 and costimulate the T cell.

"Costimulation" or a "response" by a T cell is intended to encompass T cell responses that occur upon triggering of a primary activation signal (e.g., stimulation through the CD3/TCR complex or through CD2) and a costimulatory signal in the T cell, and includes lymphokine production (e.g., IL-2 production) and T cell proliferation. Inhibition of a T cell response may involve complete blocking of the response (i.e., a lack of a response) or a reduction in the magnitude of the response (i.e., partial inhibition of the response).

A primary activation signal in a population of T cells is accomplished by contacting the T cells with an agent which stimulates a TCR/CD3 complex-associated signal in the T cells. Stimulation of the TCR/CD3 complex-associated signal in a T cell is accomplished either by ligation of the T cell receptor (TCR)/CD3 complex or the CD2 surface protein, or by directly stimulating receptor-coupled signaling pathways. Thus, an anti-CD3 antibody, an anti-CD2 antibody, or a protein kinase C activator in conjunction with a calcium ionophore is used to activate a population of T cells.

An anti-CD3 monoclonal antibody can be used to provide a primary activation signal to a population of T cells via the TCR/CD3 complex. Although a number of anti-human CD3 monoclonal antibodies are commercially available, OKT3 prepared from hybridoma cells obtained from the American Type Culture Collection or monoclonal antibody G19-4 is preferred. Similarly, binding of an anti-CD2 antibody will activate T cells. Stimulatory forms of anti-CD2 antibodies are known and available. Stimulation through CD2 with anti-CD2 antibodies is typically accomplished using a combination of at least two different anti-CD2 antibodies. Stimulatory combinations of anti-CD2 antibodies which have been described include the following: the T11.3 antibody in combination with the T11.1 or T11.2 antibody (Meuer, S. C. et al. (1984) *Cell* 36:897-906) and the 9.6 antibody (which recognizes the same epitope as T11.1) in combination with the 9-1 antibody (Yang, S. Y. et al. (1986) *J. Immunol.* 137:1097-1100). Other antibodies which bind to the same epitopes as any of the above described antibodies can also be used. Additional antibodies, or combinations of antibodies, can be prepared and identified by standard techniques.

A primary activation signal can also be delivered to a T cell through use of a combination of a protein kinase C (PKC) activator such as a phorbol ester (e.g., phorbol myristate acetate) and a calcium ionophore (e.g., ionomycin which raises cytoplasmic calcium concentrations). The use of these agents bypasses the TCR/CD3 complex but delivers a stimulatory signal to T cells. These agents are also known to exert a synergistic effect on T cells to promote T cell activation and can be used in the absence of antigen to deliver a primary activation signal to T cells.

The agent providing the primary activation signal and the agent providing the costimulatory agent can be added either in soluble form or coupled to a solid phase surface. In a preferred embodiment, the two agents are coupled to the same solid phase surface.

Soluble Forms of B7 Molecules as Costimulator

The natural ligands of CD28 can also be presented to T cells in a soluble form. Soluble forms of B7 molecules include natural B7 molecules (e.g., B7-1, B7-2), a fragment thereof, or modified form of the full length or fragment of the B7 molecule that is able to bind to CD28 and costimulate the T cell. Costimulation can be evidenced by proliferation and/or cyotkine production by T cells that have received a primary activation signal. Modifications of B7 molecules include modifications that preferably enhance the affinity of binding of B7 molecules to CD28 molecules, but also modifications that diminish or do not affect the affinity of binding of B7 molecules to CD28 molecules. Modifications of B7 molecules also include those that increase the stability of a soluble form of a B7 molecule. The modifications of B7 molecules are usually produced by amino acid substitutions, but can also be produced by linkage to another molecule.

In one specific embodiment, the soluble form of a B7 molecule is a fusion protein containing a first peptide consisting of a B7 molecule (e.g., B7-1, B7-2), or fragment thereof and a second peptide corresponding to a moiety that alters the solubility, binding, affinity, stability, or valency (i.e., the number of binding sites available per molecule) of the first peptide. Preferably, the first peptide includes an extracellular domain portion of a B7 molecule that interacts with CD28 and is able to provide a costimulatory signal as evidenced by stimulation of proliferation of T cells or secretion of cytokines from the T cells upon exposure to the B7Ig fusion protein and a primary T cell activation signal. Thus, a B7-1Ig fusion protein will comprise at least about amino acids 1-208 of B7-1 and a B7-2Ig fusion protein will comprise at least about amino acids 24-245 of B7-2.

The second peptide is a fragment of an Ig molecule, such as an Fc fragment that comprises the hinge, CH2 and CH3 regions of human IgG1 or IgG4. Several Ig fusion proteins have been previously described (see e.g., Capon, D. J. et al. (1989) *Nature* 337:525-531 and Capon U.S. Pat. No. 5,116, 964 [CD4-IgG1 constructs]; Linsley, P. S. et al. (1991) *J. Exp. Med.* 173:721-730 [a CD28-IgG1 construct and a B7-1-IgG1 construct]; and Linsley, P. S. et al. (1991) *J. Exp. Med.* 174: 561-569 [a CTLA4-IgG1]). A resulting B7Ig fusion protein (e.g., B7-1Ig, B7-2Ig) may have altered B7-2 solubility, binding affinity, stability, or valency and may increase the efficiency of protein purification. In particular fusion of a B7 molecule or portion thereof to the Fc region of an immunoglobulin molecule generally provides an increased stability to the protein, in particular in the plasma.

Fusion proteins within the scope of the invention can be prepared by expression of a nucleic acid encoding the fusion protein in a variety of different systems. Typically, the nucleic acid encoding a B7 fusion protein comprises a first nucleotide sequence encoding a first peptide consisting of a B7 molecule or a fragment thereof and a second nucleotide sequence encoding a second peptide corresponding to a moiety that alters the solubility, binding, stability, or valency of the first peptide, such as an immunoglobulin constant region. Nucleic acid encoding a peptide comprising an immunoglobulin constant region can be obtained from human immunoglobulin mRNA present in B lymphocytes. It is also possible to obtain nucleic acid encoding an immunoglobulin constant region from B cell genomic DNA. For example, DNA encoding Cγ1 or Cγ4 can be cloned from either a cDNA or a genomic library or by polymerase chain reaction (PCR) amplification in accordance standard protocols. A preferred nucleic acid encoding an immunoglobulin constant region comprises all or a portion of the following: the DNA encoding human Cγ1 (Takahashi, N. S. et al. (1982) *Cell* 29:671-679), the DNA encoding human Cγ2; the DNA encoding human Cγ3 (Huck, S., et al. (1986) *Nucl. Acid Res.* 14:1779); and the DNA encoding human Cγ4. When an immunoglobulin constant region is used in the B7 fusion protein, the constant region can be modified to reduce at least one constant region mediated biological effector function. For example, DNA encoding a Cγ1 or Cγ4 constant region can be modified by PCR mutagenesis or site directed mutagenesis. Protocols and reagents for site directed mutagenesis systems can be obtained commercially from Amersham International PLC, Amersham, UK.

In a particularly preferred embodiment of the invention, B7-1Ig and B7-2Ig fusion proteins comprise about amino acids 1-208 of B7-1 and about amino acids 24-245 of B7-2, respectively, fused to the heavy chain of IgG1.

In one embodiment the first and second nucleotide sequences are linked (i.e., in a 5' to 3' orientation by phosphodiester bonds) such that the translational frame of the B7 protein or fragment thereof and the IgC (i.e., Fc fragment that comprises the hinge, CH2, and CH3 regions of human IgG) coding segments are maintained (i.e., the nucleotide sequences are joined together in-frame). Thus, expression (i.e., transcription and translation) of the nucleotide sequence produces a functional B7Ig fusion protein. The nucleic acids of the invention can be prepared by standard recombinant DNA techniques. For example, a B7Ig fusion protein can be constructed using separate template DNAs encoding B7 and an immunoglobulin constant region. The appropriate segments of each template DNA can be amplified by polymerase chain reaction (PCR) and ligated in frame using standard techniques. A nucleic acid of the invention can also be chemically synthesized using standard techniques. Various methods of chemically synthesizing polydeoxynucleotides are known, including solid-phase synthesis which has been automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373, 071, incorporated by reference herein).

The nucleic acids encoding B7 molecules or B7Ig fusion proteins (e.g., B7-1, B7-2) can be inserted into various expression vectors, which in turn direct the synthesis of the corresponding protein in a variety of hosts, particularly eucaryotic cells, such as mammalian or insect cell culture and procaryotic cells, such as *E. coli*. Expression vectors within the scope of the invention comprise a nucleic acid as described herein and a promotor operably linked to the nucleic acid. Such expression vectors can be used to transfect host cells to thereby produce fusion proteins encoded by nucleic acids as described herein. An expression vector of the invention, as described herein, typically includes nucleotide sequences encoding a B7 molecule or B7Ig fusion protein operably linked to at least one regulatory sequence. "Operably linked" is intended to mean that the nucleotide sequence is linked to a regulatory sequence in a manner which allows expression of the nucleotide sequence in a host cell (or by a cell extract). Regulatory sequences are art-recognized and can be selected to direct expression of the desired protein in an appropriate host cell. The term regulatory sequence is intended to include promoters, enhancers, polyadenylation signals and other expression control elements. Such regulatory sequences are known to those skilled in the art and are described in Goeddel, *Gene Expression Technology: Methods in Enzymology* 185, Academic Press, San Diego, Calif. (1990). It should be understood that the design of the expression vector may depend on such factors as the choice of the host cell to be transfected and/or the type and/or amount of protein desired to be expressed.

An expression vector of the invention can be used to transfect cells, either procaryotic or eucaryotic (e.g., mammalian, insect or yeast cells) to thereby produce fusion proteins encoded by nucleotide sequences of the vector. Expression in procaryotes is most often carried out in *E. coli* with vectors containing constitutive or inducible promoters. Certain *E. coli* expression vectors (so called fusion-vectors) are designed to add a number of amino acid residues to the expressed recombinant protein, usually to the amino terminus of the expressed protein. Such fusion vectors typically serve three purposes: 1) to increase expression of recombinant protein; 2) to increase the solubility of the target recombinant protein; and 3) to aid in the purification of the target recombinant protein by acting as a ligand in affinity purification. Examples of fusion expression vectors include pGEX (Amrad Corp., Melbourne, Australia) and pMAL (New England Biolabs, Beverly, Mass.) which fuse glutathione S-tranferase and maltose E binding protein, respectively, to the target recombinant protein. Accordingly, a B7 molecule or B7Ig fusion gene may be linked to additional coding sequences in a procaryotic fusion vector to aid in the expression, solubility or purification of the fusion protein. Often, in fusion expression vectors, a proteolytic cleavage site is introduced at the junction of the fusion moiety and the target recombinant protein to enable separation of the target recombinant protein from the fusion moiety subsequent to purification of the fusion protein. Such enzymes, and their cognate recognition sequences, include Factor Xa, thrombin and enterokinase.

Inducible non-fusion expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector4 relies on host RNA polymerase transcription from the hybrid trp-lac fusion promoter. Target gene expression from the pET 11d vector relies on transcription from the T7 gn10-lac 0 fusion promoter mediated by a coexpressed viral RNA polymerase (T7 gn1). This viral polymerase is supplied by host strains BL21(DE3) or HMS174(DE3) from a resident λ prophage harboring a T7 gn1 under the transcriptional control of the lacUV 5 promoter.

One strategy to maximize expression of at B7 molecule or B7Ig fusion protein in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy would be to alter the nucleotide sequence of the B7 molecule or B7Ig fusion protein construct to be inserted into an expression vector so that the individual codons for each amino acid would be those preferentially utilized in highly expressed *E. coli* proteins (Wada et al., (1992) *Nuc. Acids Res.* 20:2111-2118). Such alteration of nucleic acid sequences are encompassed by the invention and can be carried out by standard DNA synthesis techniques.

Alternatively, a B7 molecule or B7Ig fusion protein can be expressed in a eucaryotic host cell, such as mammalian cells (e.g., Chinese hamster ovary cells (CHO) or NS0 cells), insect cells (e.g., using a baculovirus vector) or yeast cells. Other suitable host cells may be found in Goeddel, (1990) supra or are known to those skilled in the art. Eucaryotic, rather than procaryotic, expression of a B7 molecule or B7Ig may be preferable since expression of eucaryotic proteins in eucaryotic cells can lead to partial or complete glycosylation and/or formation of relevant inter- or intra-chain disulfide bonds of a recombinant protein. For expression in mammalian cells, the expression vector's control functions are often provided by viral material. For example, commonly used promoters are derived from polyoma, Adenovirus 2, cytomegalovirus and Simian Virus 40. To express a B7 molecule or B7Ig fusion protein in mammalian cells, generally COS cells (Gluzman, Y., (1981) *Cell* 23:175-182) are used in conjunction with such vectors as pCDM8 (Seed, B., (1987) *Nature* 329:840) for transient amplification/expression, while CHO (dhfr⁻ Chinese Hamster Ovary) cells are used with vectors such as pMT2PC (Kaufman et al. (1987), *EMBO* 6:187-195) for stable amplification/expression in mammalian cells. A preferred cell line for production of recombinant protein is the NS0 myeloma cell line available from the ECACC (catalog #85110503) and described in Galfre, G. and Milstein, C. ((1981) *Methods in Enzymology* 73(13):3-46; and *Preparation of Monoclonal Antibodies: Strategies and Procedures*, Academic Press, N.Y., N.Y). Examples of vectors suitable for expression of recombinant proteins in yeast (e.g., *S. cerivisae*) include pYepSec1 (Baldari. et al., (1987) *Embo J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.). Baculovirus vectors available for expression of proteins in cultured insect cells (SF 9 cells) include the pAc series (Smith et al., (1983) *Mol. Cell. Biol.* 3:2156-2165) and the pVL series (Lucklow, V. A., and Summers, M. D., (1989) *Virology* 170: 31-39).

Vector DNA can be introduced into prokaryotic or eukaryotic cells via conventional transformation or transfection techniques such as calcium phosphate or calcium chloride co-precipitation, DEAE-dextran-mediated transfection, lipofection, or electroporation. Suitable methods for transforming host cells can be found in Sambrook et al. (*Molecular Cloning: A Laboratory Manual*, $2^{nd}$ Edition, Cold Spring Harbor Laboratory press (1989)), and other laboratory textbooks.

For stable transfection of mammalian cells, it is known that, depending upon the expression vector and transfection technique used, only a small faction of cells may integrate DNA into their genomes. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker may be introduced into a host cell on the same plasmid as the gene of interest or may be introduced on a separate plasmid. Cells containing the gene of interest can be identified by drug selection (e.g., cells that have incorporated the selectable marker gene will survive, while the other cells die). The surviving cells can then be screened for production of B7 molecules or B7Ig fusion proteins by, for example, immunoprecipitation from cell supernatant with an anti-B7 monoclonal antibody.

B7 molecules or B71 g fusion proteins produced by recombinant technique may be secreted and isolated from a mixture of cells and medium containing the protein. Alternatively, the protein may be retained cytoplasmically and the cells harvested, lysed and the protein isolated. A cell culture typically includes host cells, media and other byproducts. Suitable media for cell culture are well known in the art. Protein can be isolated from cell culture medium, host cells, or both using techniques known in the art for purifying proteins.

For T cell costimulation, the soluble forms of the natural ligands for CD28 are added to the T cell culture in an amount sufficient to result in costimulation of activated T cells. The appropriate amount of soluble ligand to be added will vary with the specific ligand, but can be determined by assaying different amounts of the soluble ligand in T cell cultures and measuring the extent of costimulation by proliferation assays or production of cytokines, as described in the Examples.

Coupling of the Natural Ligands to a Solid Phase Surface

In another embodiment of the invention, a natural ligand of CD28 (B7-1, B7-2) can be presented to T cells in a form attached to a solid phase surface, such as beads. The B7 molecules, fragments thereof or modified forms thereof capable of binding to CD28 and costimulating the T cells (e.g., B7 fusion proteins) can be prepared as described for the soluble B7 forms. These molecules can then be attached to the solid phase surface via several methods. For example the B7 molecules can be crosslinked to the beads via covalent modification using tosyl linkage. In this method, B7 molecules or B7 fusion proteins are in 0.05M borate buffer, pH 9.5 and added to tosyl activated magnetic immunobeads (Dynal Inc., Great Neck, N.Y.) according to manufacturer's instructions. After a 24 hr incubation at 22° C., the beads are collected and washed extensively. It is not mandatory that immunomagnetic beads be used, as other methods are also satisfactory. For example, the B7 molecules may also be immobilized on polystyrene beads or culture vessel surfaces. Covalent binding of the B7 molecules or B7Ig fusion proteins to the solid phase surface is preferable to adsorption or capture by a secondary monoclonal antibody. B7Ig fusion proteins can be attached to the solid phase surface through anti-human IgG molecules bound to the solid phase surface. In particular, beads to which anti-human IgG molecules are bound can be obtained from Advanced Magnetics, Inc. These beads can then be incubated with the B7Ig fusion proteins in an appropriate buffer such as PBS for about an hour at 5° C., and the uncoupled B7Ig proteins removed by washing the beads in a buffer, such as PBS.

It is also possible to attach the B7 molecules to the solid phase surface through an avidin- or streptavidin-biotin complex. In this particular embodiment, the soluble B7 molecule is first crosslinked to biotin and then reacted with the solid phase surface to which avidin or streptavidin molecules are bound. It is also possible to crosslink the B7 molecules with avidin or streptavidin and to react these with a solid phase surface that is covered with biotin molecules.

The amount of B7 molecules attached to the solid phase surface can be determined by FACS analysis if the solid phase surface is that of beads or by ELISA if the solid phase surface is that of a tissue culture dish. Antibodies reactive with the B7 molecules, such as mAb BB1, mAb IT2, and mAb 133 can be used in these assays. Alternatively, CTLA4Ig can also be used for that purpose.

In a specific embodiment, the stimulatory form of a B7 molecule is attached to the same solid phase surface as the agent that stimulates the TCR/CD3 complex, such as an anti-CD3 antibody. In addition to anti-CD3, other antibodies that bind to receptors that mimic antigen signals may be used, for example, the beads or other solid phase surface may be coated with combinations of anti-CD2 and a B7 molecule. The two stimulatory molecules can be bound to the solid phase surface in various ratios, but preferably in equimolar amounts.

Production of Antibodies and Coupling of Antibodies to Solid Phase Surfaces

The term "antibody" as used herein refers to immunoglobulin molecules and immunologically active portions of immunoglobulin molecules, i.e., molecules that contain an antigen binding site which specifically binds (immunoreacts with) an antigen, such as CD3, CD28. Structurally, the simplest naturally occurring antibody (e.g., IgG) comprises four polypeptide chains, two heavy (H) chains and two light (L) chains inter-connected by disulfide bonds. It has been shown that the antigen-binding function of an antibody can be performed by fragments of a naturally-occurring antibody. Thus, these antigen-binding fragments are also intended to be designated by the term "antibody". Examples of binding fragments encompassed within the term antibody include (i) an Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment (Ward et al., (1989) *Nature* 341:544-546) which consists of a VH domain; (v) an isolated complimentarity determining region (CDR); and (vi) an F(ab')$_2$ fragment, a bivalent fragment comprising two Fab fragments linked by a disulfide bridge at the hinge region. Furthermore, although the two domains of the Fv fragment are coded for by separate genes, a synthetic linker can be made that enables them to be made as a single protein chain (known as single chain Fv (scFv); Bird et al. (1988) *Science* 242:423-426; and Huston et al. (1988) *PNAS* 85:5879-5883) by recombinant methods. Such single chain antibodies are also encompassed within the term "antibody". Preferred antibody fragments for use in T cell expansion are those which are capable of crosslinking their target antigen, e.g., bivalent fragments such as F(ab')$_2$ fragments. Alternatively, an antibody fragment which does not itself crosslink its target antigen (e.g., a Fab fragment) can be used in conjunction with a secondary antibody which serves to crosslink the antibody fragment, thereby crosslinking the target antigen. Antibodies can be fragmented using conventional techniques as described herein and the fragments screened for utility in the same manner as described for whole antibodies. An antibody of the invention is further intended to include bispecific and chimeric molecules having a desired binding portion (e.g., CD28 or CTLA-4).

The language "a desired binding specificity for an epitope", as well as the more general language "an antigen binding site which specifically binds (immunoreacts with)", refers to the ability of individual antibodies to specifically immunoreact with a T cell surface molecule, e.g., CD28 or CTLA-4. That is, it refers to a non-random binding reaction between an antibody molecule and an antigenic determinant of the T cell surface molecule. The desired binding specificity is typically determined from the reference point of the ability of the antibody to differentially bind the T cell surface molecule and an unrelated antigen, and therefore distinguish between two different antigens, particularly where the two antigens have unique epitopes. An antibody which binds specifically to a particular epitope is referred to as a "specific antibody".

"Antibody combining site", as used herein, refers to that structural portion of an antibody molecule comprised of a heavy and light chain variable and hypervariable regions that specifically binds (immunoreacts with) antigen. The term "immunoreact" or "reactive with" in its various forms is used herein to refer to binding between an antigenic determinant-containing molecule and a molecule containing an antibody combining site such as a whole antibody molecule or a portion thereof.

Although soluble forms of antibodies may be used to activate T cells, it is preferred that the anti-CD3 antibody be immobilized on a solid phase surface (e.g., beads). An antibody can be immobilized directly or indirectly by, for example, by a secondary antibody, to a solid surface, such as a tissue culture flask or bead.

Specific Methodology for Antibody Production

A. The Immunogen.

The term "immunogen" is used herein to describe a composition containing a peptide or protein as an active ingredient used for the preparation of antibodies against an antigen, e.g., a CD3, a CD28, or a CTLA-4 antigen. When a peptide or protein is used to induce antibodies it is to be understood that the peptide can be used alone, or linked to a carrier as a conjugate, or as a peptide polymer.

To generate suitable antibodies, the immunogen should contain an effective, immunogenic amount of a peptide or protein, optionally as a conjugate linked to a carrier. The effective amount of peptide per unit dose depends, among other things, on the species of animal inoculated, the body weight of the animal and the chosen immunization regimen as is well known in the art. The immunogen preparation will typically contain peptide concentrations of about 10 micrograms to about 500 milligrams per immunization dose, preferably about 50 micrograms to about 50 milligrams per dose. An immunization preparation can also include an adjuvant as part of the diluent. Adjuvants such as complete Freund's adjuvant (CFA), incomplete Freund's adjuvant (IFA) and alum are materials well known in the art, and are available commercially from several sources.

Those skilled in the art will appreciate that, instead of using natural occurring forms of the antigen, e.g., the CD3, the CD28, or the CTLA-4 antigen for immunization, synthetic peptides can alternatively be employed towards which antibodies can be raised for use in this invention. Both soluble and membrane bound forms of the protein or peptide fragments are suitable for use as an immunogen and can also be isolated by immunoaffinity purification as well. A purified form of protein, such as may be isolated as described above or as known in the art, can itself be directly used as an immunogen, or alternatively, can be linked to a suitable carrier protein by conventional techniques, including by chemical coupling means as well as by genetic engineering using a cloned gene of the protein. The purified protein can also be covalently or noncovalently modified with non-proteinaceous materials such as lipids or carbohydrates to enhance immunogenecity or solubility. Alternatively, a purified protein can be coupled with or incorporated into a viral particle, a replicating virus, or other microorganism in order to enhance immunogenicity. The protein may be, for example, chemically attached to the viral particle or microorganism or an immunogenic portion thereof.

In an illustrative embodiment, a purified CD28 protein, or a peptide fragment thereof (e.g., produced by limited proteolysis or recombinant DNA techniques) is conjugated to a carrier which is immunogenic in animals. Preferred carriers include proteins such as albumins, serum proteins (e.g., globulins and lipoproteins), and polyamino acids. Examples of useful proteins include bovine serum albumin, rabbit serum albumin, thyroglobulin, keyhole limpet hemocyanin, egg ovalbumin and bovine gamma-globulins. Synthetic polyamino acids such as polylysine or polyarginine are also useful carriers. With respect to the covalent attachment of CD28 protein or peptide fragments to a suitable immunogenic carrier, there are a number of chemical cross-linking agents that are known to those skilled in the art. Preferred cross-linking agents are heterobifunctional cross-linkers, which can be used to link proteins in a stepwise manner. A wide variety of heterobifunctional cross-linkers are known in the art, including succinimidyl 4-(N-maleimidomethyl)cyclohexane-1-carboxylate (SMCC), m-Maleimidobenzoyl-N-hydroxysuccinimide ester (MBS); N-succinimidyl (4-iodoacetyl)aminobenzoate (SIAB), succinimidyl 4-(p-maleimidophenyl) butyrate (SMPB), 1-ethyl-3-(3-dimethylaminopropyl) carbodiimide hydrochloride (EDC); 4-succinimidyl-oxycarbonyl-a-methyl-a-(2-pyridyldithio)-toluene (SMPT), N-succinimidyl 3-(2-pyridyldithio) propionate (SPDP), succinimidyl 6-[3-(2-pyridyldithio) propionate]hexanoate (LC-SPDP).

It may also be desirable to simply immunize an animal with whole cells which express a protein of interest (e.g., CD28, or CTLA-4) on their surface. Various cell lines can be used as immunogens to generate monoclonal antibodies to an antigen, including, but not limited to T cells. For example, peripheral blood T cells can be obtained from a subject which constitutively expresses CD28 or CTLA-4, but can be activated in vitro with anti-CD3 antibodies, PHA or PMA. Alternatively, an antigen specific (e.g., alloreactive) T cell clone can be activated to express CD28 or CTLA-4 by presentation of antigen, together with a costimulatory signal, to the T cell. Whole cells that can be used as immunogens to produce CD28 or CTLA-4 specific antibodies also include recombinant transfectants. For example, COS and CHO cells can be reconstituted by transfection with a CD28 or CTLA-4 cDNA to produce cells expressing CD28 or CTLA-4 on their surface. These transfectant cells can then be used as immunogens to produce anti-CD28 or anti-CTLA-4 antibodies. Other examples of transfectant cells are known, particularly eukaryotic cells able to glycosylate the CD28 protein, but any procedure that works to express transfected CD28 genes on the cell surface could be used to produce the whole cell immunogen.

Alternative to a CD28- or CTLA-4-expressing cell or an isolated CD28 or CTLA-4 protein, peptide fragments of CD28 or CTLA-4 can be used as immunogens to generate antibodies.

B. Polyclonal Antibodies.

Polyclonal antibodies to a purified protein or peptide fragment thereof can generally be raised in animals by multiple subcutaneous (sc) or intraperitoneal (ip) injections of an appropriate immunogen, such as the extracellular domain of the protein, and an adjuvant. A polyclonal antisera can be produced, for example, as described in Lindsten, T. et al. (1993) *J. Immunol.* 151:3489-3499. In an illustrative embodiment, animals are typically immunized against the immunogenic protein, peptide or derivative by combining about 1 mg to 1 mg of protein with Freund's complete adjuvant and injecting the solution intradermally at multiple sites. One month later the animals are boosted with ⅕ to ⅒ the original amount of immunogen in Freund's complete adjuvant (or other suitable adjuvant) by subcutaneous injection at multiple sites. Seven to 14 days later, the animals are bled and the serum is assayed for anti-protein or peptide titer (e.g., by ELISA). Animals are boosted until the titer plateaus. Also, aggregating agents such as alum can be used to enhance the immune response.

Such mammalian-produced populations of antibody molecules are referred to as "polyclonal" because the population comprises antibodies with differing immunospecificities and affinities for the antigen. The antibody molecules are then collected from the mammal (e.g., from the blood) and isolated by well known techniques, such as protein A chromatography, to obtain the IgG fraction. To enhance the specificity of the antibody, the antibodies may be purified by immunoaffinity chromatography using solid phase-affixed immunogen. The antibody is contacted with the solid phase-affixed immunogen for a period of time sufficient for the immunogen to immunoreact with the antibody molecules to form a solid phase-affixed immunocomplex. The bound antibodies are separated from the complex by standard techniques.

C. Monoclonal Antibodies.

The term "monoclonal antibody" or "monoclonal antibody composition", as used herein, refers to a population of antibody molecules that contain only one species of an antigen binding site capable of immunoreacting with a particular epitope of an antigen. A monoclonal antibody composition thus typically displays a single binding affinity for a particular protein with which it immunoreacts. Preferably, the monoclonal antibody used in the subject method is further characterized as immunoreacting with a protein derived from humans.

Monoclonal antibodies useful in the methods of the invention are directed to an epitope of an antigen(s) on T cells, such that complex formation between the antibody and the antigen (also referred to herein as ligation) induces stimulation and T cell expansion. A monoclonal antibody to an epitope of an antigen (e.g., CD3, CD28, or CTLA-4) can be prepared by using a technique which provides for the production of antibody molecules by continuous cell lines in culture. These include but are not limited to the hybridoma technique originally described by Kohler and Milstein (1975, *Nature* 256: 495-497), and the more recent human B cell hybridoma technique (Kozbor et al. (1983) *Immunol Today* 4:72), EBV-hybridoma technique (Cole et al. (1985), *Monoclonal Antibodies and Cancer Therapy*, Alan R. Liss, Inc., pp. 77-96), and trioma techniques. Other methods which can effectively yield monoclonal antibodies useful in the present invention include phage display techniques (Marks et al. (1992). *J. Biol. Chem.* 16007-16010).

In one embodiment, the antibody preparation applied in the subject method is a monoclonal antibody produced by a hybridoma cell line. Hybridoma fusion techniques were first introduced by Kohler and Milstein (Kohler et al. *Nature* (1975) 256:495-97; Brown et al. (1981) *J. Immunol.* 127:539-46; Brown et al. (1980) *J Biol Chem* 255:4980-83; Yeh et al. (1976) *PNAS* 76:2927-31; and Yeh et al. (1982) *Int. J. Cancer* 29:269-75). Thus, the monoclonal antibody compositions of the present invention can be produced by the following method, which comprises the steps of:

(a) Immunizing an animal with a protein (e.g., CD28 or CTLA-4) or peptide thereof. The immunization is typically accomplished by administering the immunogen to an immunologically competent mammal in an immunologically effective amount, i.e., an amount sufficient to produce an immune response. Preferably, the mammal is a rodent such as a rabbit, rat or mouse. The mammal is then maintained for a time period sufficient for the mammal to produce cells secreting antibody molecules that immunoreact with the immunogen. Such immunoreaction is detected by screening the antibody molecules so produced for immunoreactivity with a preparation of the immunogen protein. Optionally, it may be desired to screen the antibody molecules with a preparation of the protein in the form in which it is to be detected by the antibody molecules in an assay, e.g., a membrane-associated form of the antigen, e.g., the CD28 or the CTLA-4 antigen. These screening methods are well known to those of skill in the art, e.g., enzyme-linked immunosorbent assay (ELISA) and/or flow cytometry.

(b) A suspension of antibody-producing cells removed from each immunized mammal secreting the desired antibody is then prepared. After a sufficient time, the mouse is sacrificed and somatic antibody-producing lymphocytes are obtained. Antibody-producing cells may be derived from the lymph nodes, spleens and peripheral blood of primed animals. Spleen cells are preferred, and can be mechanically separated into individual cells in a physiologically tolerable medium using methods well known in the art. Mouse lymphocytes give a higher percentage of stable fusions with the mouse myelomas described below. Rat, rabbit and frog somatic cells can also be used. The spleen cell chromosomes encoding desired immunoglobulins are immortalized by fusing the spleen cells with myeloma cells, generally in the presence of a fusing agent such as polyethylene glycol (PEG). Any of a number of myeloma cell lines may be used as a fusion partner according to standard techniques; for example, the P3-NS1/1-Ag4-1, P3-x63-Ag8.653 or Sp2/O-Ag14 myeloma lines. These myeloma lines are available from the American Type Culture Collection (ATCC), Rockville, Md.

The resulting cells, which include the desired hybridomas, are then grown in a selective medium, such as HAT medium, in which unfused parental myeloma or lymphocyte cells eventually die. Only the hybridoma cells survive and can be grown under limiting dilution conditions to obtain isolated clones. The supernatants of the hybridomas are screened for the presence of antibody of the desired specificity, e.g., by immunoassay techniques using the antigen that has been used for immunization. Positive clones can then be subcloned under limiting dilution conditions and the monoclonal antibody produced can be isolated. Various conventional methods exist for isolation and purification of the monoclonal antibodies so as to free them from other proteins and other contaminants. Commonly used methods for purifying monoclonal antibodies include ammonium sulfate precipitation, ion exchange chromatography, and affinity chromatography (see, e.g., Zola et al. in *Monoclonal Hybridoma Antibodies: Techniques And Applications*, Hurell (ed.) pp. 51-52 (CRC Press 1982)). Hybridomas produced according to these methods can be propagated in vitro or in vivo (in ascites fluid) using techniques known in the art.

Generally, the individual cell line may be propagated in vitro, for example in laboratory culture vessels, and the culture medium containing high concentrations of a single specific monoclonal antibody can be harvested by decantation, filtration or centrifugation. Alternatively, the yield of monoclonal antibody can be enhanced by injecting a sample of the hybridoma into a histocompatible animal of the type used to provide the somatic and myeloma cells for the original fusion. Tumors secreting the specific monoclonal antibody produced by the fused cell hybrid develop in the injected animal. The body fluids of the animal, such as ascites fluid or serum, provide monoclonal antibodies in high concentrations. When human hybridomas or EBV-hybridomas are used, it is necessary to avoid rejection of the xenograft injected into animals such as mice. Immunodeficient or nude mice may be used or the hybridoma may be passaged first into irradiated nude mice as a solid subcutaneous tumor, cultured in vitro and then injected intraperitoneally into pristane primed, irradiated nude mice which develop ascites tumors secreting large amounts of specific human monoclonal antibodies.

Media and animals useful for the preparation of these compositions are both well known in the art and commercially available and include synthetic culture media, inbred mice and the like. An exemplary synthetic medium is Dulbecco's minimal essential medium (DMEM; Dulbecco et al. (1959) *Virol.* 8:396) supplemented with 4.5 gm/l glucose, 20 mM glutamine, and 20% fetal caf serum. An exemplary inbred mouse strain is the Balb/c.

D. Combinatorial Antibodies.

Monoclonal antibody compositions of the invention can also be produced by other methods well known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies (for descriptions of combinatorial antibody display see e.g., Sastry et al. (1989) *PNAS* 86:5728; Huse et al. (1989) *Science* 246:1275; and Orlandi et al. (1989) *PNAS* 86:3833). After immunizing an animal with an appropriate immunogen (e.g., CD3, CD28) as described above, the antibody repertoire of the resulting B-cell pool is cloned. Methods are generally known for directly obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable regions from a number of murine antibodies (Larrick et al. (1991) *Biotechniques* 11:152-156). A similar strategy can also been used to amplify human heavy and light chain variable regions from human antibodies (Larrick et al. (1991) *Methods: Companion to Methods in Enzymology* 2:106-110).

In an illustrative embodiment, RNA is isolated from activated B cells of, for example, peripheral blood cells, bone marrow, or spleen preparations, using standard protocols (e.g., U.S. Pat. No. 4,683,202; Orlandi, et al. *PNAS* (1989) 86:3833-3837; Sastry et al., *PNAS* (1989) 86:5728-5732; and Huse et al. (1989) *Science* 246:1275-1281.) First-strand cDNA is synthesized using primers specific for the constant region of the heavy chain(s) and each of the κ and λ light chains, as well as primers for the signal sequence. Using variable region PCR primers, the variable regions of both heavy and light chains are amplified, each alone or in combination, and ligated into appropriate vectors for further manipulation in generating the display packages. Oligonucleotide primers useful in amplification protocols may be unique or degenerate or incorporate inosine at degenerate positions. Restriction endonuclease recognition sequences may also be incorporated into the primers to allow for the cloning of the amplified fragment into a vector in a predetermined reading frame for expression.

The V-gene library cloned from the immunization-derived antibody repertoire can be expressed by a population of display packages, preferably derived from filamentous phage, to form an antibody display library. Ideally, the display package comprises a system that allows the sampling of very large variegated antibody display libraries, rapid sorting after each affinity separation round, and easy isolation of the antibody gene from purified display packages. In addition to commercially available kits for generating phage display libraries (e.g., the Pharmacia *Recombinant Phage Antibody System*, catalog no. 27-9400-01; and the Stratagene *SurfZAP™ phage display kit, catalog no.* 240612), examples of methods and reagents particularly amenable for use in generating a variegated antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J.* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982.

In certain embodiments, the V region domains of heavy and light chains can be expressed on the same polypeptide, joined by a flexible linker to form a single-chain Fv fragment, and the scFV gene subsequently cloned into the desired expression vector or phage genome. As generally described in McCafferty et al., *Nature* (1990) 348:552-554, complete $V_H$ and $V_L$ domains of an antibody, joined by a flexible $(Gly_4-Ser)_3$ linker can be used to produce a single chain antibody which can render the display package separable based on antigen affinity. Isolated scFV antibodies immunoreactive with the antigen can subsequently be formulated into a pharmaceutical preparation for use in the subject method.

Once displayed on the surface of a display package (e.g., filamentous phage), the antibody library is screened with the protein, or peptide fragment thereof, to identify and isolate packages that express an antibody having specificity for the protein. Nucleic acid encoding the selected antibody can be recovered from the display package (e.g., from the phage genome) and subcloned into other expression vectors by standard recombinant DNA techniques.

E. Hybridomas and Methods of Preparation.

Hybridomas useful in the present invention are those characterized as having the capacity to produce a monoclonal antibody which will specifically immunoreact with an antigen of interest, e.g., a CD3, a CD28, or a CTLA-4 antigen. Methods for generating hybridomas that produce, e.g., secrete, antibody molecules having a desired immunospecificity, e.g., having the ability to immunoreact with the CD28 or CTLA-4 antigen, and/or an identifiable epitope of CD28 or CTLA-4 are known in the art. Particularly applicable is the hybridoma technology described by Niman et al. (1983) *PNAS* 80:4949-4953; and by Galfre et al. (1981) *Meth. Enzymol.* 73:3-46.

F. Chimeric and Humanized Anti-CD28 or Anti-CTLA4 Antibodies.

When antibodies produced in non-human subjects are used therapeutically in humans, they are recognized to varying degrees as foreign and an immune response may be generated in the patient. One approach for minimizing or eliminating this problem, which is preferable to general immunosuppression, is to produce chimeric antibody derivatives, i.e., antibody molecules that combine a non-human animal variable region and a human constant region. Such antibodies are the equivalents of the monoclonal and polyclonal antibodies described above, but may be less immunogenic when administered to humans, and therefore more likely to be tolerated by the patient.

Chimeric mouse-human monoclonal antibodies (i.e., chimeric antibodies) reactive with CD28 or CTLA4 can be produced by recombinant DNA techniques known in the art. For example, a gene encoding the constant region of a murine (or other species) anti-CD28 or anti-CTLA4 antibody molecule is substituted with a gene encoding a human constant region (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., PCT Application WO 86/01533; Cabilly et al. U.S. Pat. No. 4,816,567; Cabilly et al., European Patent Application 125,023; Better et al. (1988 *Science* 240:1041-1043); Liu et al. (1987) *PNAS* 84:3439-3443; Liu et al. (1987) *J. Immunol.* 139:3521-3526; Sun et al. (1987) *PNAS* 84:214-218; Nishimura et al. (1987) *Canc. Res.* 47:999-1005; Wood et al. (1985) *Nature* 314:446-449; and Shaw et al. (1988) *J. Natl Cancer Inst.* 80:1553-1559).

A chimeric antibody can be further "humanized" by replacing portions of the variable region not involved in antigen binding with equivalent portions from human variable regions. General reviews of "humanized" chimeric antibodies are provided by Morrison, S. L. (1985) *Science* 229:1202-1207 and by Oi et al. (1986) *BioTechniques* 4:214. Those methods include isolating, manipulating, and expressing the nucleic acid sequences that encode all or part of an immunoglobulin variable region from at least one of a heavy or light chain. Sources of such nucleic acid are well known to those skilled in the art and, for example, may be obtained from an anti-CD28 or anti-CTLA4 antibody producing hybridoma. The cDNA encoding the chimeric antibody, or fragment thereof, can then be cloned into an appropriate expression vector. Suitable "humanized" antibodies can be alternatively produced by CDR or CEA substitution (see U.S. Pat. No. 5,225,539 to Winter; Jones et al. (1986) *Nature* 321:552-525; Verhoeyan et al. (1988) *Science* 239:1534; and Beidler et al. (1988) *J. Immunol.* 141:4053-4060).

As an alternative to humanizing an mAb from a mouse or other species, a human mAb directed against a human protein can be generated. Transgenic mice carrying human antibody repertoires have been created which can be immunized with human CD28 or CTLA4. Splenocytes from these immunized transgenic mice can then be used to create hybridomas that secrete human mAbs specifically reactive with human CD28 or CTLA4 (see, e.g., Wood et al. PCT publication WO 91/00906, Kucherlapati et al. PCT publication WO 91/10741; Lonberg et al. PCT publication WO 92/03918; Kay et al. PCT publication 92/03917; Lonberg, N. et al. (1994) *Nature* 368: 856-859; Green, L. L. et al. (1994) *Nature Genet.* 7:13-21; Morrison, S. L. et al. (1994) *Proc. Natl. Acad. Sci. USA* 81:6851-6855; Bruggeman et al. (1993) *Year Immunol* 7:33-40; Tuaillon et al. (1993) *PNAS* 90:3720-3724; Bruggeman et al. (1991) *Eur. J. Immunol.* 21:1323-1326).

Agents which Act Intracellularly to Stimulate a Signal Associated with CD28 Ligation In another embodiment of the invention, a CD28-associated signal is provided by contacting T cells with an agent which acts intracellularly to stimulate a signal in the T cell mediated by ligation of CD28. The term "agent", as used herein, is intended to encompass chemicals and other pharmaceutical compounds which stimulate a costimulatory or other signal in a T cell without the requirement for an interaction between a T cell surface receptor and a costimulatory molecule or other ligand. For example, the agent may act intracellularly to stimulate a signal associated with CD28 ligation. In one embodiment, the agent is a non-proteinaceous compound. As the agent used in the method is intended to bypass the natural receptor:ligand stimulatory mechanism, the term agent is not intended to include a cell expressing a natural ligand. Natural ligands for CD28 include members of the B7 family of proteins, such as B7-1 (CD80) and B7-2 (CD86).

It is known that CD28 receptor stimulation leads to the production of D-3 phosphoinositides in T cells and that inhibition of the activity of phosphatidylinositol 3-kinase (PI3K) in a T cell can inhibit T cell responses, such as lymphokine production and cellular proliferation. Protein tyrosine phosphorylation has also been shown to occur in T cells upon CD28 ligation and it has been demonstrated that a protein tyrosine kinase inhibitor, herbimycin A, can inhibit CD28-induced IL-2 production (Vandenberghe, P. et al. (1992) *J. Exp. Med.* 175:951-960; Lu, Y. et al. (1992) *J. Immunol.* 149:24-29). Thus, the CD28 receptor mediated pathway can be stimulated by is contacting T cells with an activator of PI3K or an agent which stimulates protein tyrosine phosphorylation in the T cell, or both. An activator of PI3K can be identified based upon its ability to stimulate production of at least one D-3 phosphoinositide in a T cell. The term "D-3 phosphoinositide" is intended to include derivatives of phosphatidylinositol that are phosphorylated at the D-3 position of the inositol ring and encompasses the compounds phosphatidylinositol(3)-monophosphate (PtdIns(3)P), phosphatidylinositol(3,4)-bisphosphate (PtdIns(3,4)$P_2$), and phosphatidylinositol(3,4,5)-trisphosphate (PtdIns(3,4,5)$P_3$). Thus, in the presence of a PI3K activator, the amount of a D-3 phosphoinositide in the T cell is increased relative to the amount of the D-3 phosphoinositide in the T cell in the absence of the substance. Production of D-3 phosphoinositides (e.g., PtdIns (3)P, PtdIns(3,4)$P_2$ and/or PtdIns(3,4,5)$P_3$) in a T cell can be assessed by standard methods, such as high pressure liquid chromatography or thin layer chromatography, as discussed above. Similarly, protein tyrosine phosphorylation can be stimulated in a T cell, for example, by contacting the T cell with an activator of protein tyrosine kinases, such as pervanadate (see O'Shea, J. J. et al. (1992) *Proc. Natl. Acad. Sci. USA* 89:10306-103101; and Secrist, J. P. (1993) *J. Biol. Chem.* 268:5886-5893). Alternatively, the T cell can be contacted with an agent which inhibits the activity of a cellular protein tyrosine phosphatase, such as CD45, to increase the net amount of protein tyrosine phosphorylation in the T cell.

Uses of the Invention

An individual infected with HIV can be treated in vivo or ex vivo by contacting T cells of the individual with an agent which stimulates (e.g., anti-CD28 antibody) or allows stimulation of (e.g., soluble anti-CTLA4 antibody or fragment thereof) a CD28-associated signal in the T cell, thereby downregulating an HIV-1 fusion cofactor, such as CCR5. The agent which provides a primary activation signal can be administered to the individual, or it can be an agent which is already in the individual, such as one or more antigens.

The invention further provides methods for vaccination of an individual against infection by HIV. Accordingly, in one embodiment of the invention, an agent which downregulates expression of an HIV-1 fusion cofactor by stimulating or allowing stimulation of a CD28-associated signal, such as an immobilized anti-CD28 or anti-CTLA-4 antibody, is administered to an individual prior to a viral infection. The method can further comprise administration to the individual of an agent which provides a primary activation signal to the T cells (e.g., an anti-CD3 antibody).

The invention is particularly useful for treating subjects suffering from chronic HIV-1 infection. Stimulation of the CD28 receptor leads to an upregulation of β-chemokines, such as RANTES, MIP-1α, and MIP-1β (described in, for example, Reily, J. L. et al. (1997) *J. Immunol.* 158:5545-53). The increased secretion of these chemokines can, in turn, benefit neighboring cells by preventing further infection. Thus, the method of the invention can further be used to upregulate β-chemokines, thereby inhibiting HIV infection of bystander cells.

In other preferred embodiments, the agent which stimulates or allows stimulation of a CD28-associated signal to thereby downregulate an HIV-1 fusion cofactor, e.g., CCR5, can be coadministered with another treatment. For example, the agent can be coadministered with an influenza vaccine. Preferred agents for use in this embodiment are anti-CTLA-4 antibodies (preferably soluble) or fragments thereof (preferably Fab fragments) which inhibit binding of B7 molecules to CTLA4, but allow B7 molecules, such as B7 molecules on antigen-presenting cells, to provide costimulation to T cells via CD28 crosslinking, in the context of presentation of viral antigen (such anti-CTLA4 antibodies and fragments thereof are described in, for example, Krummel, M. F. et al. (1995) *Int. Immunol.* 8(4):519-23).

Compositions and Kits

This invention also provides compositions and kits comprising an agent which stimulates or allows stimulation of an accessory molecule on the surface of T cells (e.g., an anti-CD28 or an anti-CTLA-4 antibody) coupled to a solid phase surface in an amount sufficient to down regulate expression of an HIV-1 fusion cofactor (e.g., CCR5), and, optionally, including an agent which stimulates a TCR/CD3 complex-associated signal in T cells (e.g., an anti-CD3 antibody) coupled to the same or different solid phase surface. For example, the composition can comprise an anti-CD28 and an anti-CD3 antibody coupled to the same solid phase surface (e.g., a bead). Alternatively, the composition can include an agent which stimulates an accessory molecule on the surface of T cells coupled to a first solid phase surface and an agent which stimulates a TCR/CD3 complex-associated signal in T cells coupled to a second solid phase surface. For example, the composition can include an anti-CD28 coupled to a first bead and an anti-CD3 antibody coupled to a second bead. Another embodiment of the invention provides compositions including an effective amount of an anti-CTLA-4 antibody (preferably in soluble form) or a fragment thereof (e.g., a Fab fragment). Kits comprising such compositions and instructions for use are also within the scope of this invention.

Methods for Identifying Agents Which Modulate Expression of an HIV-1 Fusion Cofactor Another aspect of the invention pertains to screening assays for identifying inhibitors and activators of expression of an HIV-1 fusion cofactor, such as CCR5, in a cell following stimulation or inhibition of one or more intracellular signals which result from ligation of a surface receptor on the cell which binds a costimulatory molecule, such as CD28. In one embodiment, a T cell which expresses a cell surface receptor (e.g., CD28 or CTLA-4) which binds a costimulatory molecule is utilized. To identify an inhibitor of expression of an HIV-1 fusion cofactor, such as CCR5, an intracellular signal transduction pathway associated with the receptor in the T cell (e.g., CD28) is stimulated in the presence of an agent to be tested and an inhibitor is identified based upon its ability inhibit or downregulate expression of the HIV-1 fusion cofactor in the T cell.

A costimulatory signal can be stimulated in the T cell by contacting the T cell with a ligand for CD28 or CTLA-4. The ligand can be a physiologic ligand, such as membrane-bound B7-1 or B7-2, or an antibody directed against the T cell surface receptor. A cell which naturally expresses B7-1 and/or B7-2 can be used or more preferably a cell (e.g., a CHO cell) which is transfected to express a costimulatory molecule is used. In the presence of an inhibitor, stimulation of a T cell through a surface receptor which binds a costimulatory molecule (e.g., CD28) results in downregulation or a reduction in the levels of CCR5 RNA in the T cell relative to stimulation in the absence of the inhibitor. RNA levels in the T cell can be measured by any suitable method known in the art, such as those described in the Examples section. For example, RNA expression (e.g., CCR5 RNA) can be detected using Northern blots, in situ hybridization, or RNA-based polymerase chain reaction. Alternatively, a specific protein product can be detected by Western blot. Preferably, the detection technique will be quantitative or at least semi-quantitative.

In one embodiment, mRNA is obtained from a sample of cells, and transcripts encoding an HIV-1 fusion cofactor are detected. To illustrate, an initial crude cell suspension, such as may be obtained from dispersion of a sample, is sonicated or otherwise treated to disrupt cell membranes so that a crude cell extract is obtained. Known techniques of biochemistry (e.g., preferential precipitation of proteins) can be used for initial purification if desired. The crude cell extract, or a partially purified RNA portion therefrom, is then treated to further separate the RNA. For example, crude cell extract can be layered on top of a 5 ml cushion of 5.7 M CsCl, 10 mM Tris-HCl, pH 7.5, 1 mM EDTA in a 1 in.×3½ in. nitrocellulose tube and centrifuged in an SW27 rotor (Beckman Instruments Corp., Fullerton, Calif.) at 27,000 rpm for 16 hrs at 15° C. After centrifugation, the tube contents are decanted, the tube is drained, and the bottom 0.5 cm containing the clear RNA pellet is cut off with a razor blade. The pellets are transferred to a flask and dissolved in 20 ml 10 mM Tris-HCl, pH 7.5, 1 mm EDTA, 5% sarcosyl and 5% phenol. The solution is then made 0.1 M in NaCl and shaken with 40 ml of a 1:1 phenol:chloroform mixture. RNA is precipitated from the aqueous phase with ethanol in the presence of 0.2 M Na-acetate pH 5.5 and collected by centrifugation. Any other method of isolating RNA from a cellular source may be used instead of this method. Other mRNA isolation protocols, such as the Chomczynski method (described in U.S. Pat. No. 4,843,155), are known in the art.

The mRNA must be isolated from the source cells under conditions which preclude degradation of the mRNA. The action of RNase enzymes is particularly to be avoided because these enzymes are capable of hydrolytic cleavage of the RNA nucleotide sequence. A suitable method for inhibiting RNase during extraction from cells involves the use of 4 M guanidium thiocyanate and 1 M mercaptoethanol during the cell disruption step. In addition, a low temperature and a pH near 5.0 are helpful in further reducing RNase degradation of the isolated RNA.

In certain embodiments, the next step may be to form DNA complementary to the isolated heterogeneous sequences of mRNA. The enzyme of choice for this reaction is reverse transcriptase, although in principle any enzyme capable of forming a faithful complementary DNA copy of the mRNA template could be used. The cDNA transcripts produced by the reverse transcriptase reaction are somewhat heterogeneous with respect to sequences at the 5' end and the 3' end due to variations in the initiation and termination points of individual transcripts, relative to the mRNA template. The variability at the 5' end is thought to be due to the fact that the oligo-dT primer used to initiate synthesis is capable of binding at a variety of loci along the polyadenylated region of the mRNA. Synthesis of the cDNA transcript begins at an indeterminate point in the poly-A region, and variable length of poly-A region is transcribed depending on the initial binding site of the oligo-dT primer. It is possible to avoid this indeterminacy by the use of a primer containing, in addition to an oligo-dT tract, one or two nucleotides of the RNA sequence itself, thereby producing a primer which will have a preferred and defined binding site for initiating the transcription reaction.

In an exemplary embodiment, there is provided a nucleic acid composition comprising a (purified) oligonucleotide probe including a region of nucleotide sequence which is capable of hybridizing to a sense or antisense sequence of an HIV-1 fusion cofactor (e.g., CCR5) transcript. The nucleic acid of a cell is rendered accessible for hybridization, the probe is exposed to nucleic acid of the sample, and the hybridization of the probe to the sample nucleic acid is detected. Such techniques can be used to quantitatively determine mRNA transcript levels.

In certain embodiments, detection of the such transcripts utilizes a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1944) *PNAS* 91:360-364). In an illustrative embodiment, the method includes the steps of (i) collecting a sample of cells from a patient, (ii) isolating nucleic acid (e.g., mRNA) from the cells of the sample, (iii) contacting the nucleic acid sample (or optionally a cDNA preparation derived therefrom) with one or more primers which specifically hybridize to a CCR5 transcript, for example, under conditions such that hybridization and amplification of at least a portion of the transcript (if present) occurs, and (iv) detecting the presence or absence of an amplification product.

Detection and/or amplification can be carried out with a probe which, for example, hybridizes under stringent conditions to a nucleic acid encoding the transcript of interest. For detection, the probe preferably further comprises a label group attached to the nucleic acid and able to be detected.

In yet another embodiment, the assay detects the presence or absence of an HIV-1 fusion cofactor (e.g., CCR5) in cells of the cell sample, e.g., by determining the level of the protein by an immunoassay, gel electrophoresis or the like.

This invention is further illustrated by the following Examples which should not be construed as limiting. The contents of all references and published patent applications cited throughout this application are hereby incorporated by reference. The following methodology described in the Materials and Methods section was used throughout the examples set forth below.

EXAMPLES

Materials and Methods

Antibodies and Reagents

The following monoclonal antibodies were used to stimulate cells: anti-CD3 OKT3 (mouse IgG2a, American Type Tissue Collection), anti-CD28 9.3 (mouse IgG2a, (Hansen, J. A., 1980. Immunogenetics 10:247), anti-CD2 35.1 (mouse IgG2a, American Type Tissue Collection), anti-CD4 G17-2 (mouse IgG1, (Ledbetter, J. A., 1987. Mol. Immunol. 24:1255)), anti-CD5 10.2 (mouse IgG2a, (Martin, P. J., 1980. Immunogenetics 1 1:429)), and anti-monomorphic HLA class I mAb W6/32 (IgG2a, American Type Tissue Collection).

Cell Separation and Stimulation

Peripheral blood lymphocytes were isolated by Percoll gradient centrifugation from leukopacks obtained by apheresis of healthy donors. CD4+ T cells were purified by negative selection as described previously (June, C. H., 1987 *Mol. Cell. Biol.* 7:4472). The purity of the CD4 cells was monitored after each apheresis. The cell preparations were 88 to 98% pure for CD4 cells, and were found to contain less than 5% CD8 cells. CD8 cells were purified in a similar manner with the addition of a positive selection step using Dynal Detach-A-Bead®. (Dynal, Great Neck, N.Y.).

Purified cells were cultured at $1 \times 10^6$ cells/ml in RPMI with 10% FCS (Hyclone, Logan, Utah), 20 mM HEPES, 2 mM glutamine, 50 µg/ml of gentamicin (Biofluids, Rockville, Md.). Cells were stimulated with either 5 µg/ml of PHA (Sigma, St. Louis, Mich.) and 100 units of IL-2 (Boehringer Mannheim, Indianapolis, Ind.) or Dynal M-450 antibody coated beads using 1 bead per cell (Dynal, Great Neck, N.Y.). Magnetic polystryrene beads were coated via tosyl conjugation (Levine, B. L., (1996) *Science* 272:1939) with equal amounts of anti-CD3 plus anti-CD28 monoclonal antibody, anti-CD3 plus anti-CD2 monoclonal antibody, anti-CD3 plus anti-CD4 monoclonal antibody, anti-CD3 plus anti-CD5 monoclonal antibody or anti-CD3 plus anti-MHC I monoclonal antibody. The cell cultures were fed every 2-3 days with fresh medium to maintain a concentration of 1×106 cells/ml.

Conditioned medium was collected from companion cultures of autologous cells that were set up in parallel and not infected with HIV-1. The conditioned medium was subjected to centrifugation, and the supernatant was added to a 50% final concentration. In some experiments, NAbs to C—C chemokines were added to the conditioned medium as described above.

Acute Infection Procedure

In order to further dissect the mechanisms of the CD28 antiviral effect, we have developed a quantitative acute infection system measuring virus and cells to study antiviral effects. Purified peripheral blood CD4 cells were activated by various mitogenic stimulants. In all experiments presented herein, flow cytometric analysis of the cell populations revealed <5% contamination with CD8 cells. Macrophage-tropic strains of HIV-1 were used to infect purified CD4 cells. Viral stocks were prepared exclusively by passage on PBMC. Viral growth was quantitated by assay for HIV-1 gag as previously described (Levine, B. L., (1996) *Science* 272:1939).

Cell growth was quantitated by enumeration of cells and cell volume. IL-2 was added to the culture medium in all conditions to assure similar cellular growth rates. To address specificity of the CD28 effect, polystyrene beads were coated with anti-CD3 mAb OKT3 to deliver a signal through the T cell receptor. Costimulatory signals were provided by preparing beads coated with equivalent amounts of anti-CD28 mAb 9.3. Cells were pelleted and washed with RPMI with 10% FCS and the supernatant (CM) was saved. Cells were infected in a 0.4 ml volume containing 50% appropriate CM and approximately $1 \times 10^4$ TCID$_{50}$ DNAse-treated HIV-1$_{us-1}$ (Mascola, J. R., 1994 J. Infect. bis. 169:48) or HIV-1$_{Ba-L}$ (Gartner, S. (1986) *Science* 233:215) was added. After 2 hours at 37° C., the cell/virus mixture was washed 3 times with RPMI+10% FCS to remove residual inoculum and the cells were refed with 50% CM to a concentration of $1 \times 10^6$ cells/ml. After 3 days, the cells were counted and sized again and refed with either RPMI with 10% FCS or 50% CM, if the experiment warranted that a heterologous CM be maintained in the culture, to a concentration of $1 \times 10^6$/ml. $1 \times 10^6$ cells were removed from the cultures at the various time points mentioned in the figure legends and pelleted and the supernatants were saved for p24 analysis. The cell pellets were washed once with HBSS and frozen.

PCR\Liquid Hybridization Assay

A quantitative PCR was used to measure HIV-1 proviral DNA. The assay is sensitive to about 5 copies per $10^5$ cells (Levine, B. L. (1996) *Science* 272:1939). Frozen cell pellets containing $1 \times 10^6$ cells were resuspended in 100:1 lysis buffer [10 mM Tris-HCl, (pH7.5), 2.5 mM MgCl2, 0.45% Triton X-100 (Boehringer Mannheim), 0.45% Tween 20 (Biorad), and 0.12 mg/ml proteinase K (Boehringer Mannheim)]). HIV-1 gag DNA sequences were amplified from crude lystates as described (Levine, B. L. (1996) *Science* 272:1939). The amplified products were detected by liquid hybridization with end-labelled oligonucleotide probes, followed by gel electrophoresis. PCR products were quantitated as described (Levine, B. L. et al.) using a Molecular Dynamics phosphorimager. Copy number was determined by comparison to plasmid standards and data presented was found to be linear to 10,000 copies of gag. To standardize cell pellets, human β-globin sequences were amplified from a 1/20 dilution of the crude lysates as described (Vahey, M. T. 1995. Quantitative Liquid Hybridization PCR Method Employing Storage Phosphor Technology. In PCR Primer: A Laboratory Manual. C. W. Dieffenbach and G. S. Dveksler, eds. Cold Spring Harbor Laboratory Press, p. 313).

Chemokine, Lymphokine, and p24 Assays

Using appropriate dilutions of culture supernatants, MIP-1α, MIP-1β, RANTES, IFN-γ, and p24 were assayed with R&D Systems (Minneapolis, Minn.), Endogen (Cambridge, Mass.), and Coulter (Kendall, Fla.) ELISA kits according to the manufacturer's instructions.

Example 1

Production and Screening of Anti-CTLA4 Monoclonal Antibodies

Production of Monoclonal Antibodies to Human CTLA4

BALB/c female mice (obtained from Taconic, Germantown, N.Y.) can be immunized subcutaneously and intraperitoneally with either 50 mg per mouse of recombinant human *E. coli-expressed* CTLA4 (extracellular domain only) emulsified in complete Freund's adjuvant (Sigma Chemical Company, St. Louis, Mo.) for ER series mice or $2 \times 10^6$ PMA/ionomycin-activated human T cells (obtained from Leukopaks) per mouse for ES series mice. The mice can then be boosted with 20-25 mg/mouse human recombinant CTLA4 emulsified in incomplete Freund's adjuvant (Sigma Chemical Company, St. Louis, Mo.) or $10^6$ PMA/ionomycin-activated human T cells at 14 day intervals following the initial immunizations. The mice are bled from the tail vein and the sera assayed for the presence of antibodies reactive to the immunogen by ELISA against the immunizing protein. Mice showing a strong serological titre are boosted intravenously with 50 mg recombinant human CTLA4 per mouse diluted in phosphate-buffered saline, pH 7.2 (GIBCO, Grand Island, N.Y.). Three to four days following the boost, the spleens from these mice are fused at a 5:1 ratio with SP 2/0-Ag 14 myeloma cells (ATCC, Rockville. MD) with PEG 1450 (ATCC, Rockville. MD) and plated onto 96 well plates containing irradiated MRC-5 fibroblast cells (ATCC, Rockville. MD) in Dulbecco's modified Eagle's media (GIBCO, Grand Island, N.Y.) containing 25 CPSR-3 (Sigma Chemical Company), 2 mM L-glutamine, 50 U/ml penicillin, 50 mg/ml streptomycin, 20 mg/ml gentamycin, 0.25 mg/ml fungizone, and 10% NCTC-109 (GIBCO, Grand Island, N.Y.). Selection of hybridomas can be done in the presence of hypoxanthineaminopterin-thymidine (ATCC, Rockville. MD). As hybridoma colonies grow out in the next 10-21 days, supernatant from the wells is screened on 96 well flat-bottomed EIA plates (Costar, Cambridge, Mass.) coated with recombinant human CTLA4 as a primary screen. Secondary screening is done by flow cytometry on human CTLA4-transfected CHO cells and PMA/ionomycin activated human T cells. Hybridoma supernatants identified as containing antibodies directed towards CTLA4 are expanded and subcloned twice prior to ascites production and antibody purification by Protein A-Sepharose affinity chromatography.

Primary Screening of mAbs: ELISA Protocol

Each well of a 96 well flat bottomed EIA plate (Costar, Cambridge, Mass.) can be coated with 50 ml per well of a 1 mg/ml recombinant human CTLA4 solution made in phosphate-buffered saline, pH 7.2, overnight at 4° C. The CTLA4 solution is aspirated off and the wells were blocked with 100 ml of 1% BSA in phosphate-buffered saline, pH 7.2 for 1 hour at room temperature. Following this blocking incubation, the wells are washed 3× with phosphate-buffered saline, pH 7.2 and 50 ml hybridoma supernatant is added per well and incubated 45 minutes at 37° C. Following this incubation, the wells are washed 3× with phosphate-buffered saline, pH 7.2 and then incubated with 50 ml per well of a 1:4000 dilution of horseradish peroxidase-conjugated affinity purified Goat anti-Mouse IgG (H&L) specific antibodies (Zymed Laboratories, San Francisco, Calif.) for 45 minutes at 37° C. The wells are then washed 3× with phosphate-buffered saline, pH 7.2 followed by a 30 minute incubation in 50 ml per well of 1 mM ABTS (2,2 azino-bis-3-ethylbenzthiazole-6-sulfonic acid) in 0.1 M sodium citrate, pH 4.2, to which a 1:1000 dilution of 30% hydrogen peroxide has been added as a substrate for the HRP to detect bound antibody. The absorbance is then determined at 410 nm on a spectrophotometer (Molecular Devices Corp, Menlo Park, Calif.).

Secondary Screening of mAbs: Flow Cytometry

Secondary screening can be done by flow cytometry on human CTLA4-gpi-transfected CHO cells and PMA/ionomycin activated human T cells. CTLA4 is expressed on CHO and COS cells by linking the extracellular domain of CTLA4 to a glycophosphatidylinositol (gpi) anchor. DNA encoding the extracellular domain of CTLA4 can be amplified from a human CTLA4 cDNA by PCR using as sense primer, CAT-GAAGCTTCTCGAGCCGCCACCAT GGCTTGCCT-TGGA (SEQ ID NO: 2), containing a Hind III site, a strong translational start site, and the first 15 nucleotides of the CTLA4 coding sequence and an antisense primer, GAGAAT-TCTAGACTAGCTTAAGTCAGAATCTGGGCACGGT (SEQ ID NO: 3), containing the last 19 nucleotides of the CTLA4 extracellular domain and an Afl II site. PCR conditions were 94°, 1 min, 43°,1 min, 72°, 1 min for 35 cycles followed by one cycle of 72° for 10 min. The PCR product can be digested with Hind III and Afl II, gel purified, and ligated into a Hind III and Afl II digested pCDM8 vector containing the gpi anchor of human CD58 (see *J. Immunol.* 148:3271, kindly provided by Dr. Donald Staunton, Center for Blood Research, Boston, Mass.). Plasmid containing the CTLA4-gpi insert are transiently transfected into COS cells and strongly expressed cell surface CTLA4, as judged by binding of B7-Ig fusion protein. The CTLA4-gpi plasmid is cotransfected into CHO cells with a plasmid encoding neomycin resistance and stable transfectants are selected with G418. CHO cell transfectants are sorted on the basis of B7-Ig binding and cloned.

Cells for flow cytometry (either CHO-CTLA4 or activated human T cells) are washed thoroughly in 1% BSA in phosphate-buffered saline, pH 7.2, then incubated with 50 ml hybridoma supernatant or culture media per $10^6$ cells for 30 minutes at 4° C. Following the incubation, the cells are washed 3× with 1% BSA in phosphate-buffered saline, pH 7.2, then incubated in 50 ml of a 1:40 dilution of fluorescein conjugated Goat anti-Mouse IgG (H&L) antibodies (Zymed Laboratories, San Francisco, Calif.) for 30 minutes at 4° C. The cells are then washed 3× in 1% BSA in phosphate-buffered saline, pH 7.2 and fixed in 1% paraformaldehyde solution. The cell samples are then analyzed on a FACScan flow cytometer (Becton Dickinson, San Jose, Calif.).

Example 2

Characterization of Anti-CTLA4 Monoclonal Antibodies

Binding Specificity

To determine the binding specificity of the CTLA-4 mAbs, their binding to either CHO cells transfected to express CD28 or CHO cells transfected to express CTLA-4 is assessed by indirect immunofluorescence. The binding pattern of the different anti-CTLA4 mAbs is then compared to a control, e.g., anti-CD28 mAb 3D10.

Example 3

The CD28 Antiviral Effect is Restricted to M-Tropic Isolates of HIV-1

Purified CD4+ lymphocytes were obtained from uninfected donors as described in, for example, C. H. June et al. (1987) *Mol. Cell. Biol.* 7:4474, and B. L. Levine et al. 1995. *Int. Immunol.* 7:891 (1995). The purified cells were stimulated with DYNAL® M-450 beads coated via tosyl conjugation with equal quantities of αCD3 (OKT3, mouse IgG2a, American Type Tissue Collection), and αCD28 (9.3, mouse IgG2a) (4). Alternatively, purified CD4+ cells were stimulated with phytohemagglutinin [PHA, 5 µg/ml (Sigma)] and 100 units/ml IL-2 (Boehringer Mannheim). Three days after stimulation, $7 \times 10^6$ CD4 cells stimulated with αCD3/αCD28 (open symbols; FIG. 1) or PHA/IL-2 (filled symbols; FIG. 1) were infected with $1 \times 10^4$ $TCID_{50}$ (median tissue culture infectious dose) of $HIV_{US1}$ (squares; FIG. 1) or with $1 \times 10^4$ MAGI (described in, for example, J. Kimpton, et al. (1992) *J. Virol.* 66:2232) infectious doses of $HIV_{NL4-3}$ (circles; FIG. 1).

After 2 hours at 37° C., the cells were washed three times and refed with 50% conditioned medium to a final concentration of $1\times10^6$ cells/ml. At the designated time points, cleared supernatant was analyzed for the presence of p24$_{Gag}$ antigen by ELISA (Coulter). Each experiment was done at least 5 times, and representative values are depicted.

As shown in FIG. 1, the CD28 antiviral effect is restricted to M-tropic isolates of HIV-1. Incubation of PHA/IL-2-activated CD4$^+$ cells with either HIV$_{US1}$ or HIV$_{NL4-3}$ resulted in a productive infection. When CD3/CD28-activated CD4 cells were infected with HIV$_{US1}$, P24$_{Gag}$ antigen production was virtually undetectable throughout the experiment, in agreement with a previous observation that CD3/CD28-activated cells are resistant to infection with the M-tropic isolate HIV$_{Ba-L}$ (described in B. L. Levine et al.). However, when CD3/CD28-stimulated cells were infected with the TCL-tropic isolate HIV$_{NL4-3}$, a productive infection ensued (FIG. 1).

Example 4

Only Cells Stimulated with Immobilized αCD3/αCD28 are Resistant to Infection with the M-Tropic Isolate HIV-1$_{Ba-L}$ CD28-mediated resistance to M-tropic viruses requires costimulation with bead-immobilized αCD28 because stimulation of CD4$^+$ cells with bead-immobilized αCD3 and soluble αCD28, or with bead-immobilized αCD3 and IL-2, renders the cells sensitive to infection with M-tropic viruses. To further investigate the specificity of the CD28-mediated antiviral effect, beads were prepared containing antibodies to CD3 in combination with antibodies to the cell surface coreceptors CD2, CD4, CD5, CD7 and MHC Class I. Binding of antibodies to these coreceptors in conjunction with αCD3 treatment increases cellular proliferation. Purified CD4 cells were stimulated with beads coated with αCD3 and antibodies to the various surface receptors. IL-2 was added to all cultures to ensure that all combinations of immobilized antibodies resulted in equivalent cell proliferation.

Figure 2:
FIG. 2 depicts HIV-1 gag DNA sequences present in crude cell lysates quantitated using a PCR-based assay. Purified CD4$^+$ cells were stimulated with either PHA and IL-2 (lanes 1-4), or with beads coated with equal quantities of αCD3/αCD28 (lanes 5-8), αCD3/αMHC class I (lanes 9-12), αCD3/αCD2 (lanes 13-16), αCD3/αCD4 to (lanes 17-20), αCD3/αCD5 (lanes 21-24) and αCD3/αCD7 (lanes 25-28). Three days post-stimulation, $5 \times 10^6$ CD4$^+$ cells stimulated by each method were infected with $10^4$ $TCID_{50}$ (median tissue culture infectious dose) of $HIV_{Ba-L}$. $1 \times 10^6$ cells were harvested immediately after virus addition (hour 0), post-virus washout (hour 2), and at designated time points thereafter.

As shown in FIG. 2, purified CD4$^+$ cells were stimulated with either PHA and IL-2 (lanes 1-4), or with beads coated with equal quantities of αCD3/αCD28 (lanes 5-8), αCD3/αMHC class I (lanes 9-12), αCD3/αCD2 (lanes 13-16), αCD3/αCD4 (lanes 17-20), αCD3/αCD5 (lanes 21-24) and αCD3/αCD7 (lanes 25-28). Three days post-stimulation, $5\times10^6$ CD4$^+$ cells stimulated by each method were infected with $10^4$ TCID$_{50}$ (median tissue culture infectious dose) of HIV$_{Ba-L}$. $1\times10^6$ cells were harvested immediately after virus addition (hour 0), post-virus washout (hour 2), and at designated time points thereafter. HIV-1 gag DNA sequences present in crude cell lysates were quantitated using a previously described PCR-based assay (19). Quantitative results are shown (9). All exposures were for one hour.

The results shown in FIG. 2 demonstrate that only cells stimulated with immobilized αCD3/αCD28 were resistant to infection with the M-tropic isolate HIV-1$_{Ba-L}$ (FIG. 2). Quantitative analysis indicated that the resistance was robust.

Example 5

Figure 3:
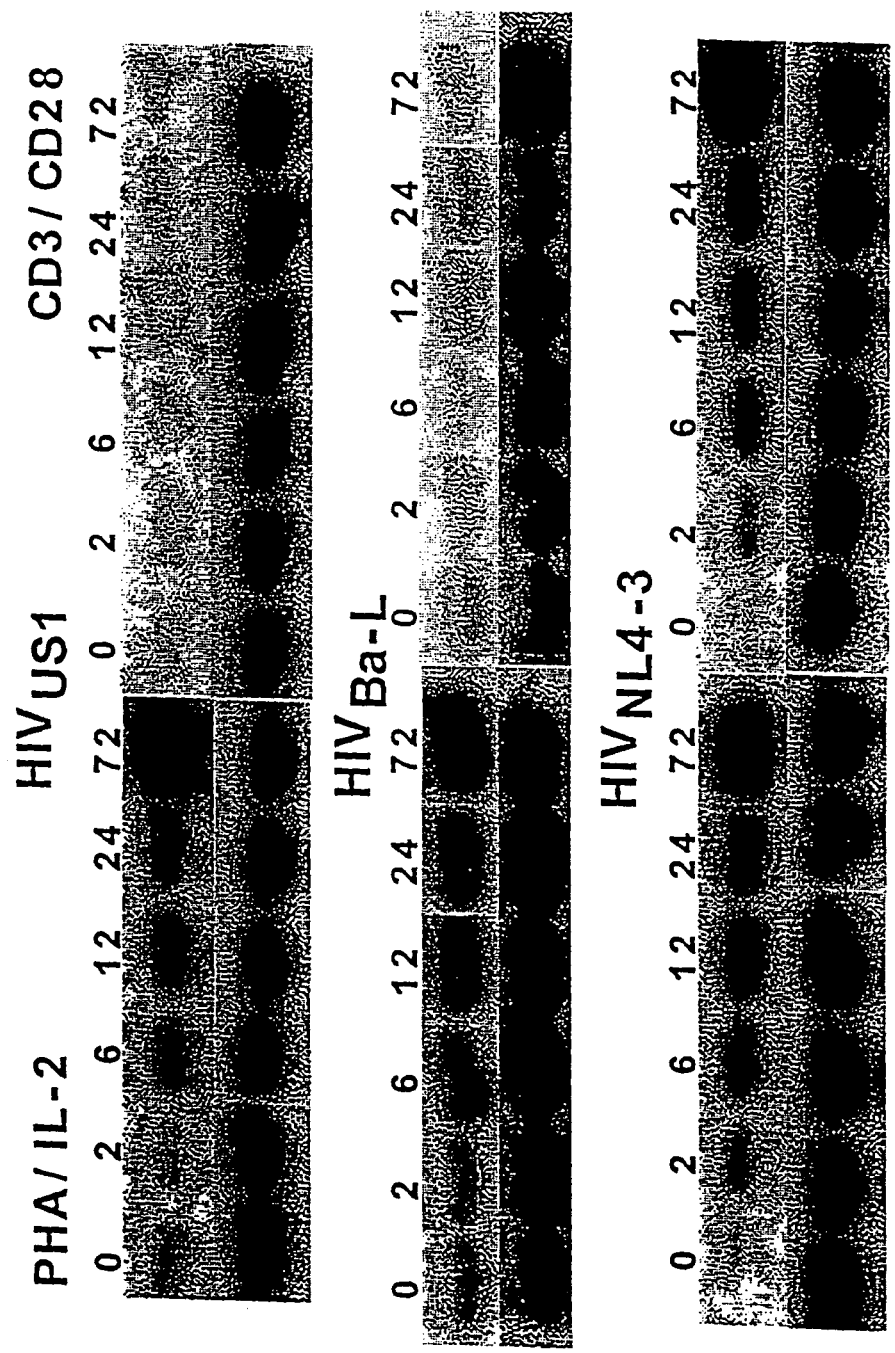
FIG. 3 depicts HIV-1 gag DNA sequences present in crude cell lysates quantitated using a PCR-based assay. Purified CD4$^+$ cells were stimulated with PHA/IL-2 (left panels) or αCD3/αCD28 (right panels) and infected with $1 \times 10^4$ $TCID_{50}$ of the M-tropic isolates $HIV_{US1}$ and $HIV_{Ba-L}$ or $1 \times 10^4$ MAGI infectious doses of the TCL-tropic isolate $HIV_{NL4-3}$. Cells were harvested immediately after infection (lanes marked 0), as well as 2, 6, 12, 24, and 72 hours after infection and HIV DNA detected.

Early Events in the Viral Replication Cycle Confirm That the CD28 Antiviral Effect is Restricted to M-Tropic Viruses To determine the nature of the M-tropic-specific block, early events in the viral replication cycle were examined by monitoring reverse transcription in HIV-1-infected CD3/CD28- and PHA/IL-2-stimulated CD4 cells (FIG. 3). Purified CD4$^+$ cells were stimulated with PHA/IL-2 (left panels) or αCD3/αCD28 (right panels) as described in FIG. 1. Three days after stimulation, $5\times10^6$ cells were infected with $1\times10^4$ TCID$_{50}$ of the M-tropic isolates HIV$_{US}$1 and HIV$_{Ba-L}$ or $1\times10^4$ MAGI infectious doses of the TCL-tropic isolate HIV$_{NL4-3}$, as described in FIG. 1. Virus stocks were treated with DNAse (Boehringer Mannheim) prior to harvesting to degrade contaminating viral DNA. Cells were harvested immediately after infection (lanes marked 0), as well as 2, 6, 12, 24, and 72 hours after infection, as indicated in the figure. HIV DNA was detected as described in FIG. 2. Early reverse transcription (strong stop) products were amplified using the following primers: 5'-GGC TAA CTA GGG AAC CCA CTG-3' (sense, SEQ ID NO:4) and 5'-CTG CTA GAG ATT TTC CAC ACT GAC-3' (antisense, SEQ ID NO:5). Products were detected by liquid hybridization with an end-labelled oligonucleotide probe (5'-CCG TCT GTT GTG TGA CTC TGG TAA CTA GAG-3', SEQ ID NO:6). The small amount of strong stop DNA present in time zero samples most likely represents reverse transcription products initiated within the virion. Input cell equivalents were standardized by amplification of human β-globin DNA sequences. Amplified β-globin DNA sequences are shown immediately underneath the HIV DNA panels.

As shown in FIG. 3, in PHA/IL-2-treated cells, strong stop DNA was detectable shortly after infection with all three viruses, and the level increased for the duration of the experiment. Furthermore, in CD3/CD28-stimulated cells infected with HIV$_{NL4-3}$, strong stop DNA products accumulated rapidly, confirming that the CD28 antiviral effect was restricted to M-tropic viruses. In contrast, little or no strong stop DNA was detected in αCD3/αCD28-treated cells infected with either HIV$_{Ba-L}$ or HIV$_{US1}$.

Example 6

The Block in the Ability of M-Tropic Viruses to Enter CD3/CD28-Stimulated Cells is at the Level of Envelope-Mediated Membrane Fusion The failure of M-tropic HIV-1 isolates to initiate reverse transcription in CD3/CD28-stimulated CD4$^+$ cells suggested that a prior event in the replication cycle, such as viral binding or entry, was impaired. Since CD3/CD28-stimulated cells and PHA/IL-2-stimulated cells express equivalent levels of surface CD4, the ability of activated CD4$^+$ T cells to support membrane fusion by envelope glycoproteins from different viral isolates was analyzed using a β-galactosidase reporter gene-based cell fusion assay (as described in, for example, C. C. Broder et al. (1995) *Proc. Natl. Acad. Sci. USA* 92:9004; and O. Nussbaum, C. C. et al. (1994) *J. Virol.* 68:5411). PHA/IL-2-stimulated CD4 cells fused with cells expressing either TCL-tropic or M-tropic HIV-1 envelopes. In contrast, whereas CD3/CD28-activated cells fused efficiently with cells expressing TCL-tropic envelopes, they failed to fuse with cells expressing M-tropic envelopes. This experiment demonstrated that the block in the ability of M-tropic viruses to enter CD3/CD28-stimulated cells was at the level of envelope-mediated membrane fusion. The high level to which CD3/CD28-stimulated cells fused with cells expressing the LAV envelope is consistent with the susceptibility of CD3/CD28-activated cells to infection by TCL-tropic isolates.

Example 7

No CCR5 Transcripts are Detected at Any Point in CD3/CD28-Stimulated Cells

Figure 4:
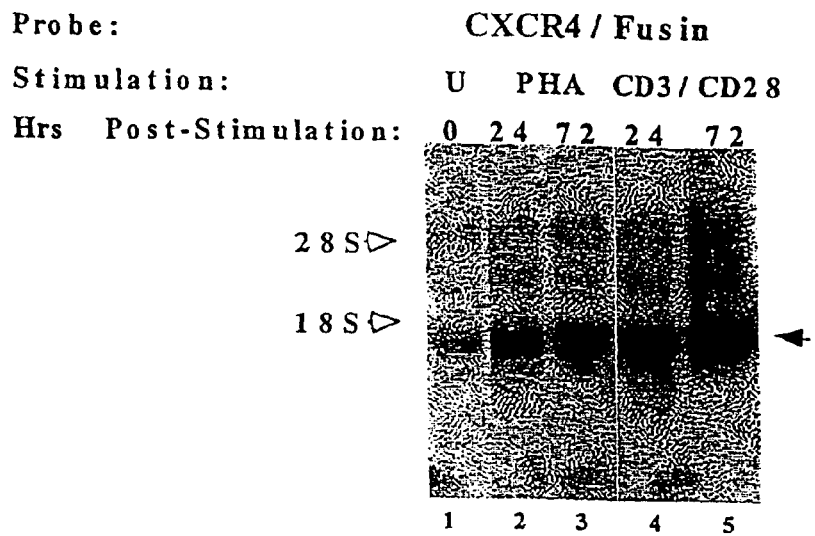
FIG. 4 is a depiction of an analysis illustrating that the expression of chemokine receptor transcripts is differentially regulated in CD3/CD28-stimulated CD4$^+$ cells. RNA was isolated from unstimulated CD4$^+$ cells (lane 1) or from CD4 cells stimulated with PHA/IL-2 (lanes 2 and 3) or αCD3/αCD28 (lanes 4 and 5) at the indicated times post-stimulation using RNAstat (Teltest). 20 µg of total RNA was separated on agarose/formaldehyde gels, and transferred to Zeta-probe membranes (BioRad). The membranes were hybridized initially with an end-labelled oligonucleotide probe specific for CCR5. The blots were stripped and then rehybridized with a random-primed 1.3 kb EcoRI CXCR4/Fusin gene fragment. The membranes were then stripped and hybridized with an end-labelled oligonucleotide probe specific for 28S ribosomal RNA and the transcripts were visualized using a Molecular Dynamics phosphorimager. The positions of 18S and 28S rRNA are indicated by open arrows, while probe-specific bands are indicated by closed arrows. The image in part (A) was obtained with a 2 hour exposure, the image in part (C) with a 10 minute exposure, while the image in part (B) was obtained with a 48 hour exposure.
Figure 4:
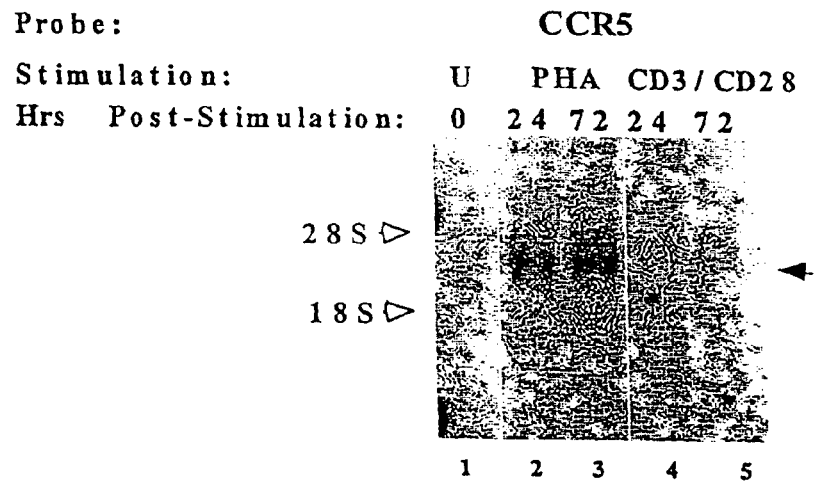
Figure 4:
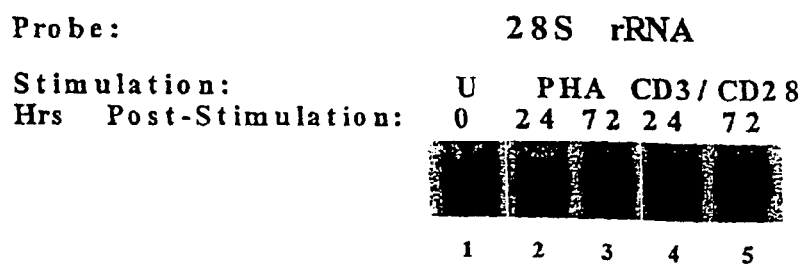

In this experiment, expression of the HIV-1 fusion cofactors CXCR4/Fusin and CCR5 for TCL-tropic and M-tropic HIV-1 isolates respectively was examined in CD4+ cells stimulated with PHA/IL-2 or αCD3/αCD28 by assaying for transcripts encoding these chemokine receptors (FIG. 4). RNA was isolated from 5×10$^7$ unstimulated CD4+ cells (lane 1) or from CD4 cells stimulated with PHA/IL-2 (lanes 2 and 3) or α CD3/αCD28 (lanes 4 and 5) at the indicated times post-stimulation using RNAstat (Teltest). 20 µg of total RNA was separated on agarose/formaldehyde gels, and transferred to Zeta-probe membranes (BioRad). The membranes were hybridized initially with an end-labelled oligonucleotide probe specific for CCR5 (5'-CTT GAT AAT CCA TCT TGT TCC ACC CTG TGC-3' SEQ ID NO:7). The sequence of the CCR5-specific oligonucleotide probe was chosen to distinguish between CCR5 and the closely related transcripts encoding CCR2A and CCR2B. The blots were stripped and then rehybridized with a random-primed 1.3 kb EcoRI CXCR4/Fusin gene fragment (described in B. Federsppiel et al., (1993) *Genomics* 16:707; H. Herzog, Y. et al. (1993) *Cell. Biol.* 12:465; E. E. Jazin et al., (1993) *Regul. Pept.* 47: 247; P. Loetscher et al., (1994) *J. Biol. Chem.* 269:232; H. Nomura, B. et al. (1993) *Int. Immunol.* 5:1239). The membranes were then stripped and hybridized with an end-labelled oligonucleotide probe specific for 28S ribosomal RNA (Clonetech), to ensure that equivalent amounts of RNA were loaded in each lane. Transcripts were visualized using a Molecular Dynamics phosphorimager. The positions of 18S and 28S rRNA are indicated by open arrows, while probe-specific bands are indicated by closed arrows. The image in part (A) was obtained with a 2 hour exposure, the image in part (C) with a 10 minute exposure, while the image in part (B) was obtained with a 48 hour exposure.

As shown in FIG. 4, CXCR4/Fusin transcripts (1.8 kb) were detected at low abundance in unstimulated CD4+ cells, and stimulation with either αCD3/αCD28 or PHA/IL-2 induced a rapid increase in CXCR4/Fusin transcript levels (FIG. 4). Transcripts encoding CCR5 were not detected in unstimulated cells. Although 4.0 kb CCR5-specific transcripts were detected shortly after PHA/IL-2 stimulation of CD4+ cells, no CCR5 transcripts were detected at any point in CD3/CD28-stimulated cells.

Example 8

Mechanism Which Accounts for the CD28 Antiviral Effect

Figure 5:
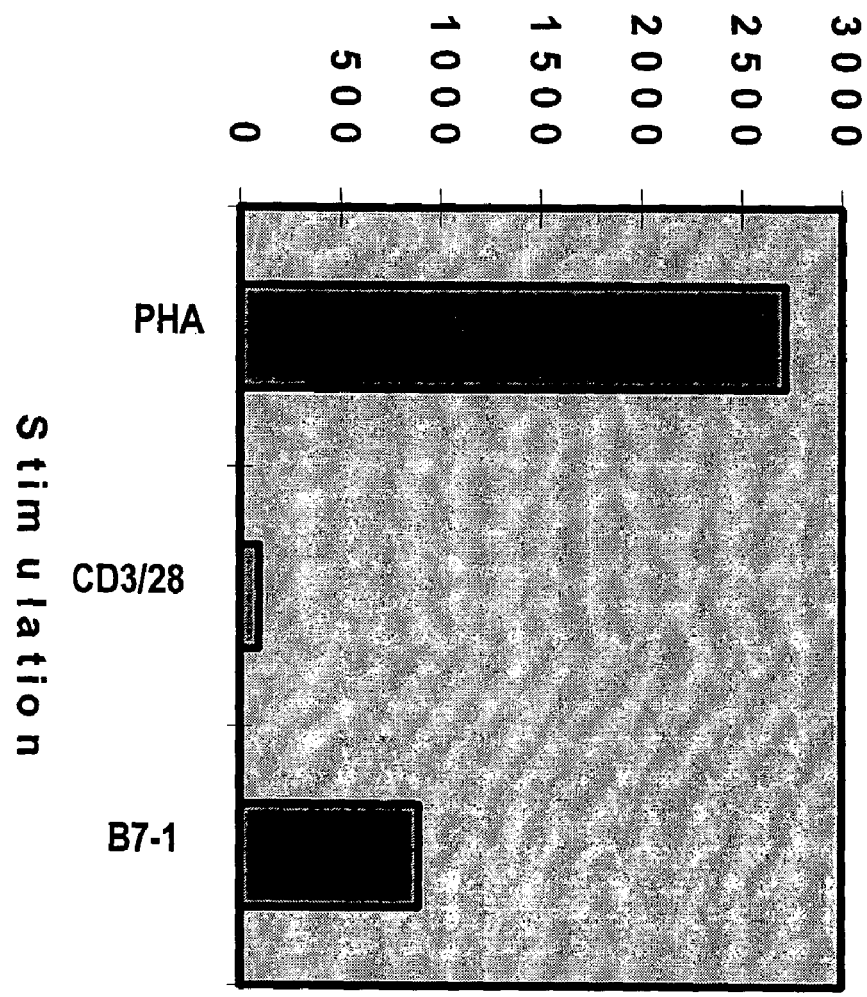
FIG. 5 is a depiction of an assay indicating that the natural ligand for CD28 permits infection with CCR5-dependent virus.
Figure 6:
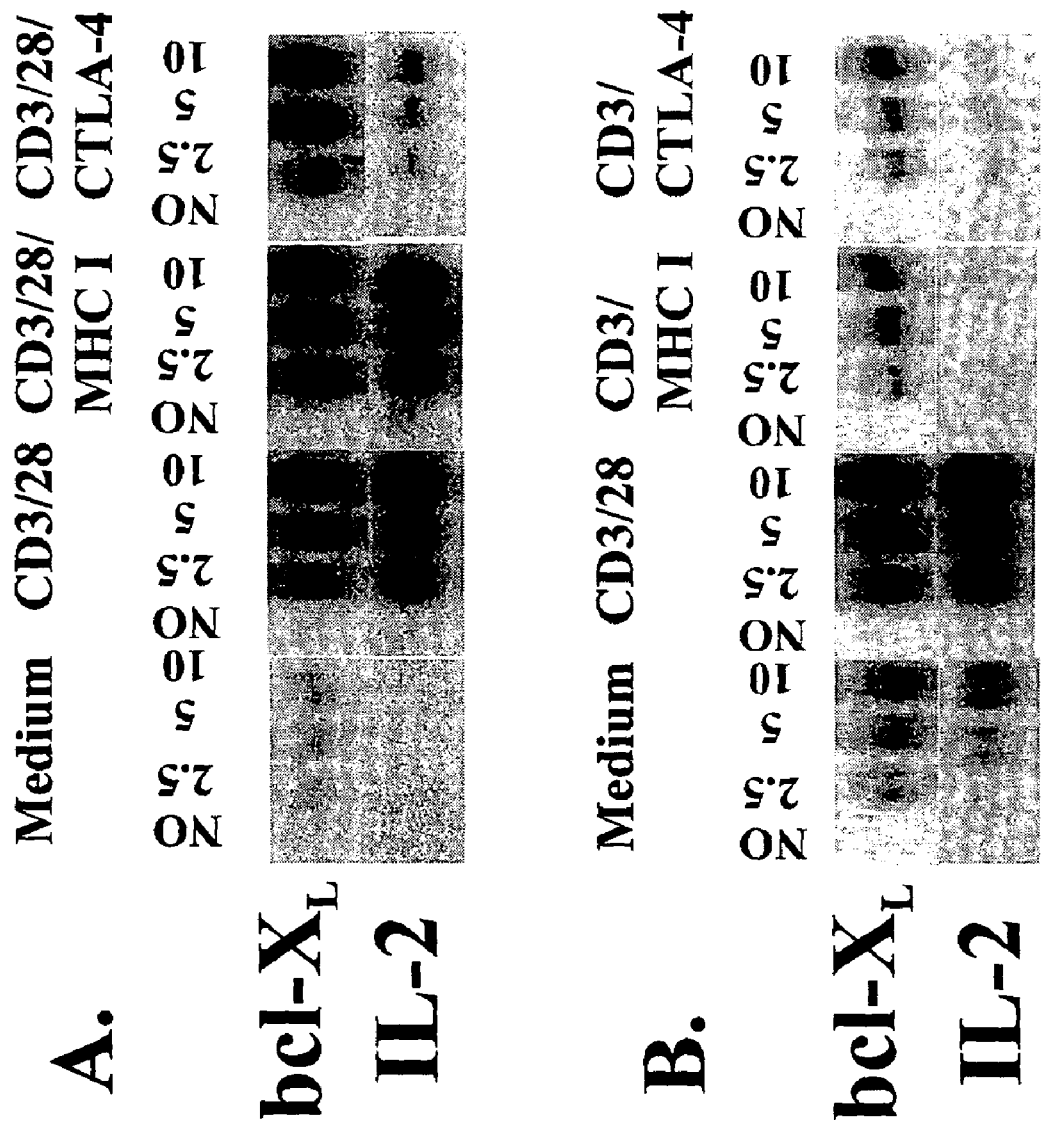
FIG. 6 is a depiction of an assay indicating that CD3, CD28, and CTLA-4 together are able to block some but not all genes induced by CD28.
Figure 7:
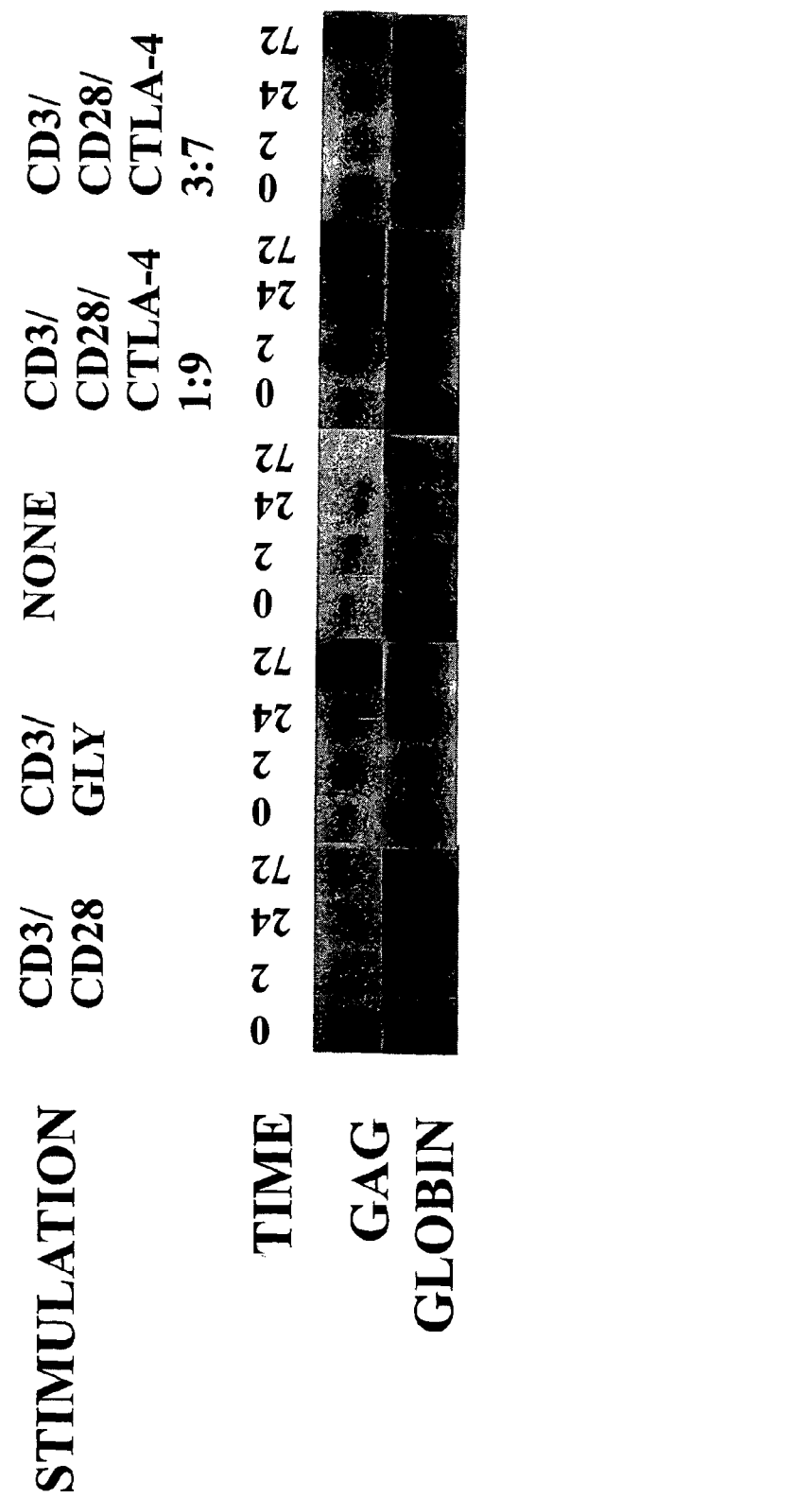
FIG. 7 is a depiction of an assay indicating that susceptibility to HIV-1 can be modulated by varying the ratio of CD28 to CTLA-4.
Figure 8:
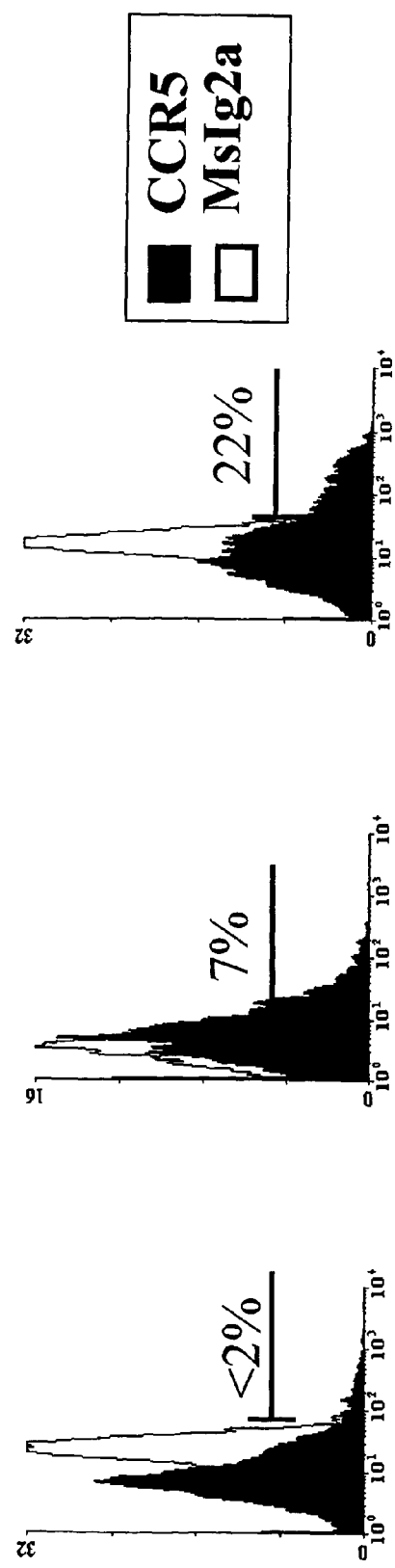
FIG. 8 is a depiction of an assay indicating that CTLA-4 reverses CD28 downregulation of CCR5.

In this example, the mechanism that accounts for the CD28 antiviral effect was studied. Using the methods described above, it was first shown that a natural ligand for CD28, e.g., B7-1, permits infection with CCR5-dependent virus (see FIG. 5). The hypothesis that B7 stimulated cells were susceptible to M-tropic HIV-1 infection because of B7-1's interaction with CTLA-4, was then studied. To do this, anti-CTLA-4 antibodies were immobilized on beads with varying amounts of anti-CD28 antibodies. The ability of these beads to mimic B7-1 stimulation was investigated using the methods described above. The results indicate that the susceptibility to HIV-1 can be modulated by varying the ratio of CD28 to CTLA-4 (bound on the bead) (see FIG. 7) and that bound CTLA-4 reverses CD28 downregulation of CCR5 (see FIG. 8) and blocks (3-chemokine production.

Figure 9:
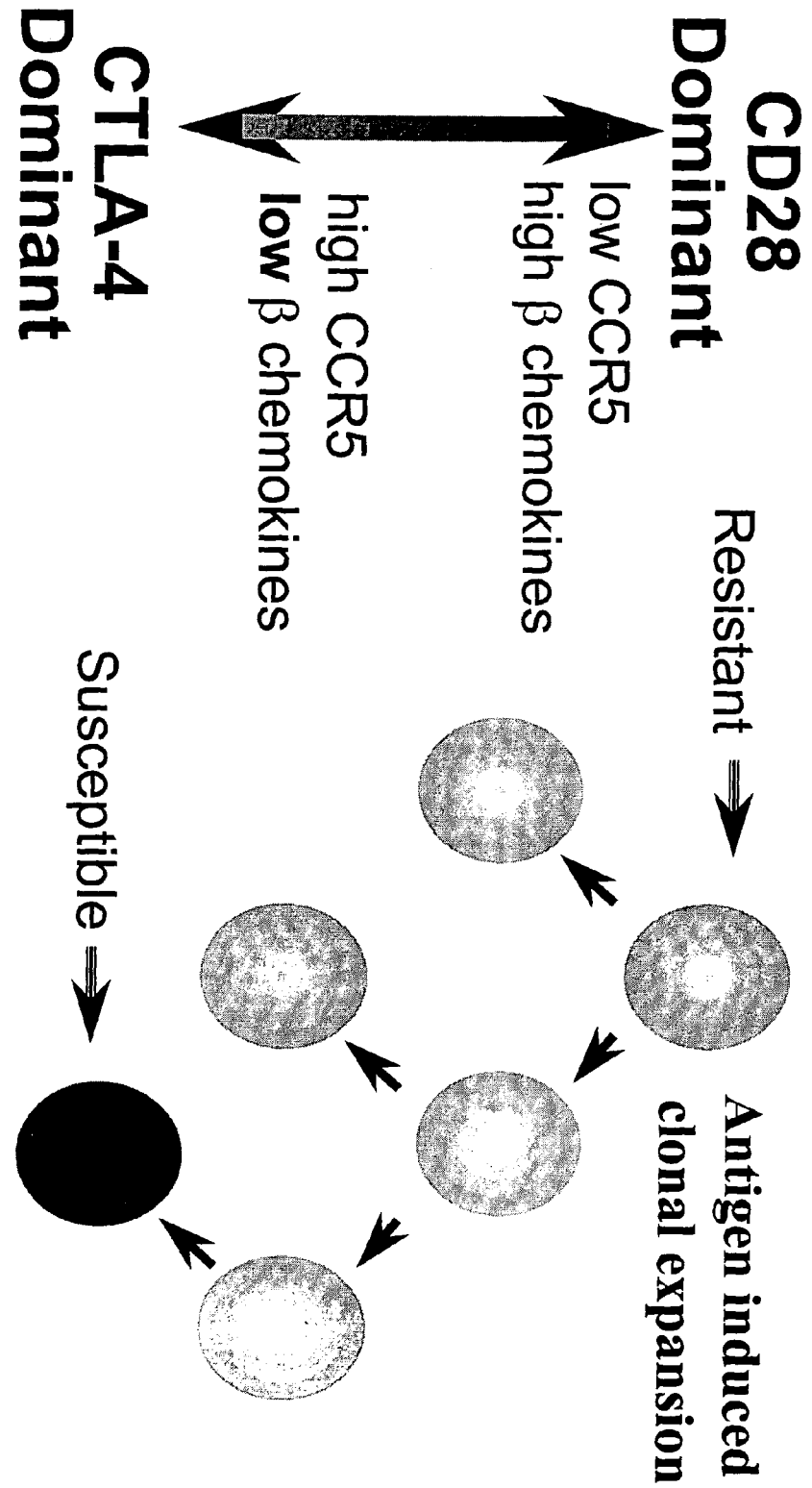
FIG. 9 is a depiction of a model indicating that the ratio of CD28 to CTLA-4 expression may be a critical determinant of susceptibility to HIV-1 infection.

Therefore, as indicated in FIG. 9, a signal through the CD28 receptor leads to downregulation of CCR5 expression and decreased susceptibility to HIV-1 infection, and a signal through the CTLA-4 receptor leads to upregulation of CCR5 expression and increased susceptibility to HIV-1 infection.

The above described results in experiments #3-7 indicate that the susceptibility of CD3/CD28-stimulated cells to TCL-tropic viruses results from upregulation of CXCR-4/Fusin mRNA expression, consistent with the high level of fusion between CD3/CD28-stimulated cells and cells expressing TCL-tropic envelope glycoproteins. Furthermore, the resistance of CD3/CD28-activated cells to infection by M-tropic viruses and primary isolates of HIV-1 correlates with the absence of detectable CCR5 mRNA expression. This is consistent with the inability of CD3/CD28-stimulated cells to fuse with cells expressing M-tropic envelope glycoproteins.

Although the mechanism by which CCR5 expression is inhibited in CD3/CD28-stimulated CD4 cells is unknown, CD28 costimulation exerts many effects on gene expression in general and cytokine expression in particular. CD28-induced down regulation of β-chemokine receptors may be a general feature in T cells, as Loetscher and colleagues recently reported that costimulation of CD4+ cells with αCD3/CD28 induced the down regulation of CCR1 and CCR2. In recent studies we have found that CD3/CD28-stimulated CD4 cells produced high levels of β-chemokines in comparison to lectin-stimulated cells, and that the levels are similar to cells stimulated with a variety of costimuli such as CD3/CD5. Thus, high levels of β-chemokines are not sufficient to mediate down regulation of CCR5. Together, these results indicate that chemokine receptor expression is regulated by distinct forms of T cell activation and that chemokine receptor expression is not a consequence of T cell activation in general.

The progression to AIDS is associated with a shift from an M-tropic to a TCL-tropic viral phenotype. Although the selective forces driving this phenotypic transition are not well defined, T cell activation itself could be a selective force. CD3/CD28-stimulated CD4+ cells may exert selective pressure in favor of TCL-tropic isolate production through the combination of high levels of β-chemokine production and lack of CCR5 expression. Presumably antigen/B7 stimulated CD4 T cells have a similar M-tropic resistance phenotype. At least early in infection, selective forces other than the susceptibility phenotype of CD4+ target cells may be dominant, as individuals who are homozygous for a defective allele of CCR5 remain resistant to infection and heterozygotes are suggested to have a delayed progression of infection. These findings may have important consequences for immune reconstitution or gene therapy initiatives in HIV-infected individuals.

Stimulation of cells with immobilized antibodies to CD3 and CD28 permits the large scale ex vivo expansion of primary CD4+ cells, thus removing one of the largest obstacles to gene therapy or immune replacement therapy for HIV-1-infected individuals. Indeed, persistent increased CD4 counts and a lack of spikes in viral load has been noted in a clinical trial that is currently in progress to test the CD28 antiviral effect in patients with intermediate stage HIV infection. The work presented herein demonstrates that lymphocyte proliferation and HIV-1 fusion cofactor expression can be unlinked.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. An ex vivo method for downregulating CCR5 expression in a T cell comprising contacting the T cell with at least one bead said bead comprising anti-CD28 antibody or antigen binding fragments and an anti-CD3 antibody or antigen binding fragments, both immobilized on said bead; and measuring the level of CCR5 RNA or protein expression in said contacted T cell, wherein the level of CCR5 expression in said contacted T cell is lower than the level of the CCR5 expression in a T cell not contacted with said bead.

2. A method for downregulating CCR5 RNA or protein expression in a T cell, comprising contacting the T cell in vivo with at least one bead said bead comprising an anti-CD28 antibody or antigen binding fragments and an anti-CD3 antibody or antigen binding fragments, both immobilized on said bead; and measuring the level of CCR5 RNA or protein expression in said contacted T cell, wherein the level of CCR5 RNA or protein expression in said contacted T cell is lower than the level of the CCR5 RNA or protein expression in a T cell not contacted with said bead.

3. The method of any one of claim 1 or 2, wherein the anti-CD3 antibody is an anti-human CD3 monoclonal antibody.

4. The method of any one of claim 1 or 2, wherein the anti-CD28 antibody is an anti-human CD28 monoclonal antibody.

5. The method of any one of claim 1 or 2, wherein the anti-CD3 antibody or antigen binding fragments and the anti-CD28 antibody or antigen binding fragments are coupled to the bead via a covalent modification.

6. The method of any one of claim 1 or 2, wherein the anti-CD3 antibody or antigen binding fragments and the anti-CD28 antibody or antigen binding fragments are coupled to the bead via an avidin-biotin complex.

7. The method of any one of claim 1 or 2, wherein the anti-CD3 antibody and the anti-CD28 antibody are directly coupled to the bead.

8. The method of any one of claim 1 or 2, wherein the bead is a biodegradable bead.

9. The method of any one of claim 1 or 2, wherein the bead is a magnetic bead.

10. The method of any one of claim 1 or 2, wherein the anti-CD28 antibody or antigen binding fragments and the anti-CD3 antibody or antigen binding fragments, are coupled to the same bead.

11. The method of any one of claim 1 or 2, wherein the T cells comprise HIV-infected T cells.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 45 amino acids
      (B) TYPE: amino acid
      (D) TOPOLOGY: linear (ii) MOLECULE TYPE: peptide (v) FRAGMENT TYPE: internal (ix) FEATURE:
      (A) NAME/KEY: Peptide
      (B) LOCATION: 1 - 20
      (D) OTHER INFORMATION: /note= "any 20 Xaas at location
         1 - 20 may be absent and intended to equal a range of
         0 - 20 amino acids"

(ix) FEATURE:
      (A) NAME/KEY: Peptide
      (B) LOCATION: 26 - 45
      (D) OTHER INFORMATION: /note= "any 20 Xaas at location
         26 - 45 may be absent and intended to equal a range
         of 0 - 20 amino acids"

(xi) SEQUENCE DESCRIPTION: SEQ ID NO:1:

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Pro Pro Tyr Tyr Leu Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa
        35                  40                  45
```

(2) INFORMATION FOR SEQ ID NO:2:

(i) SEQUENCE CHARACTERISTICS:
      (A) LENGTH: 39 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

CATGAAGCTT CTCGAGCCGC CACCATGGCT TGCCTTGGA                              39

(2) INFORMATION FOR SEQ ID NO:3:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:3:

GAGAATTCTA GACTAGCTTA AGTCAGAATC TGGGCACGGT                              40

(2) INFORMATION FOR SEQ ID NO:4:

(i) SEQUENCE CHARACTERISTICS:
      (A) LENGTH: 21 base pairs
      (B) TYPE: nucleic acid

```
            (C) STRANDEDNESS: single
            (D) TOPOLOGY: linear (ii) MOLECULE TYPE: cDNA (xi) SEQUENCE DESCRIPTION: SEQ ID NO:4:

GGCTAACTAG GGAACCCACT G                                                    21

(2) INFORMATION FOR SEQ ID NO:5:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:5:

CTGCTAGAGA TTTTCCACAC TGAC                                                 24

(2) INFORMATION FOR SEQ ID NO:6:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:6:

CCGTCTGTTG TGTGACTCTG GTAACTAGAG                                           30

(2) INFORMATION FOR SEQ ID NO:7:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:7:

CTTGATAATC CATCTTGTTC CACCCTGTGC                                           30
```